United States Patent
Gerbo et al.

(10) Patent No.: US 11,064,871 B2
(45) Date of Patent: Jul. 20, 2021

(54) FLEXIBLE ENDOSCOPE

(71) Applicants: Nicholas Matthew Gerbo, New Orleans, LA (US); George Gary Ventrella, New Orleans, LA (US)

(72) Inventors: Nicholas Matthew Gerbo, New Orleans, LA (US); George Gary Ventrella, New Orleans, LA (US)

(*) Notice: Subject to any disclaimer, the term of this patent is extended or adjusted under 35 U.S.C. 154(b) by 371 days.

(21) Appl. No.: 15/553,927

(22) PCT Filed: Feb. 26, 2016

(86) PCT No.: PCT/US2016/019960
§ 371 (c)(1),
(2) Date: Aug. 25, 2017

(87) PCT Pub. No.: WO2016/138495
PCT Pub. Date: Sep. 1, 2016

(65) Prior Publication Data
US 2018/0125339 A1    May 10, 2018

Related U.S. Application Data

(60) Provisional application No. 62/126,219, filed on Feb. 27, 2015.

(51) Int. Cl.
*A61B 1/005*    (2006.01)
*A61B 1/00*    (2006.01)
(Continued)

(52) U.S. Cl.
CPC ............ *A61B 1/005* (2013.01); *A61B 1/0011* (2013.01); *A61B 1/0051* (2013.01);
(Continued)

(58) Field of Classification Search
CPC ..... A61B 1/005; A61B 1/0051; A61B 1/0052; A61B 1/0053; A61B 1/0055;
(Continued)

(56) References Cited

U.S. PATENT DOCUMENTS 6,146,355 A    11/2000  Biggs
6,454,703 B1*  9/2002  Ide ...................... A61B 1/0055
                                                600/142

(Continued)

FOREIGN PATENT DOCUMENTS

CN        103220994 A    7/2013
EP          1737335 B1    5/2013

OTHER PUBLICATIONS

PCT Application No. US2016/019960; International Search Report and Written Opinion of the International Searching Authority for Applicant Nicholas Matthew Gerbo, et al, dated Jul. 12, 2016.
(Continued)

*Primary Examiner* — Ryan N Henderson
(74) *Attorney, Agent, or Firm* — Jones Walker LLP

(57) ABSTRACT

An endoscope includes a handle connected to a flexible, steerable, kink-resistant insertion tube. An endoscope insertion tube may include a shaft, a lower durometer section proximate to a distal end of the shaft, and a higher durometer section positioned between the lower durometer section and a medium durometer section. The endoscope insertion tube may further include a fourth thermoplastic laminate section proximate to a proximal end of the shaft and having a higher durometer. A method of making an endoscope insertion tube may include inserting a mandrel with one, two, or more lateral slots and a liner into a shaft, wherein the liner is positioned between the mandrel and the shaft, bonding a bonded portion of the liner to an inner surface of the shaft, separating other portion(s) of the liner from the shaft, and
(Continued)

inserting a first deflection wire in a gap between the shaft and the unbonded portion(s) of the liner.

13 Claims, 9 Drawing Sheets

(51) Int. Cl.
    *A61B 1/012*     (2006.01)
    *A61B 1/01*     (2006.01)
    *A61M 25/01*     (2006.01)

(52) U.S. Cl.
    CPC ...... *A61B 1/00064* (2013.01); *A61B 1/00071* (2013.01); *A61B 1/01* (2013.01); *A61B 1/012* (2013.01); *A61M 25/0141* (2013.01)

(58) Field of Classification Search
    CPC ... A61B 1/0056; A61B 1/0057; A61B 1/0058; A61B 1/008; A61B 2017/00305; A61B 2017/00309; A61B 2017/00314; A61B 2017/00318; A61B 2017/00323; A61B 2017/00327; A61B 2017/00331; A61M 25/0133; A61M 25/0136; A61M 25/0138; A61M 25/0141; A61M 25/0144; A61M 25/0147; A61M 25/0152; A61M 2025/0161
    See application file for complete search history.

(56) References Cited

U.S. PATENT DOCUMENTS

| | | | |
|---|---|---|---|
| 6,458,076 B1 | 10/2002 | Pruitt | |
| 6,464,632 B1 | 10/2002 | Taylor | |
| 6,921,363 B2* | 7/2005 | Knowles | A61B 8/12 600/139 |
| 6,979,312 B2 | 12/2005 | Shimada | |
| 2002/0028984 A1* | 3/2002 | Hayakawa | A61B 1/005 600/139 |
| 2005/0131279 A1* | 6/2005 | Boulais | A61B 1/0052 600/141 |
| 2006/0200000 A1* | 9/2006 | Sato | A61B 1/0056 600/146 |
| 2006/0252992 A1* | 11/2006 | Mitsumori | A61B 1/005 600/139 |
| 2008/0177144 A1* | 7/2008 | Otawara | G02B 23/2461 600/157 |
| 2008/0214897 A1* | 9/2008 | Matsuo | A61B 1/0055 600/139 |
| 2009/0030280 A1* | 1/2009 | Matsumoto | A61B 1/00071 600/121 |
| 2010/0130823 A1* | 5/2010 | Ando | A61B 1/00078 600/141 |
| 2010/0168519 A1* | 7/2010 | Matsuo | A61B 1/0055 600/139 |
| 2012/0209073 A1 | 8/2012 | McWeeney et al. | |
| 2012/0238952 A1* | 9/2012 | Mitchell | A61B 1/0057 604/95.04 |
| 2013/0050457 A1* | 2/2013 | Murayama | A61B 1/0008 348/75 |
| 2013/0338467 A1 | 12/2013 | Grasse et al. | |
| 2015/0230692 A1* | 8/2015 | Matsuda | A61B 1/005 600/104 |
| 2015/0305598 A1* | 10/2015 | Yamashita | A61B 1/0055 604/95.04 |
| 2016/0074621 A1* | 3/2016 | Yao | A61M 25/0021 604/508 |

OTHER PUBLICATIONS

PCT Application No. US2016/019960; International Preliminary Report on Patentability for Applicant Nicholas Matthew Gerbo, et al dated Aug. 29, 2017.

Hubosky, Scott G., Amar J. Raval, and Demetrius H. Bagley. "Locked deflection during flexible ureteroscopy: incidence and elucidation of the mechanism of an underreported complication." Journal of Endourology 29.8 (2015): 907-912.

* cited by examiner

FLEXIBLE ENDOSCOPE

RELATED APPLICATION

Pursuant to 35 U.S.C. § 371, this application claims priority to International App. No. PCT/US2016/19960, filed on Feb. 26, 2016, which claimed the benefit of U.S. Provisional Application No. 62/126,219, filed Feb. 27, 2015, both of which are hereby incorporated by reference.

BACKGROUND

This disclosure generally relates to insertion tubes, particularly (but without limitation) insertion tubes for endoscopes.

Flexible endoscopes are used to navigate, visualize, and operate within a variety of complex anatomies. Endoscopes may be designed to be strong, flexible, steerable, and pushable and transmit torque. They should resisting crushing and kinking. To operate, endoscopes should house imaging and working channels and deflection wires. Accordingly, conventional designs are often small, fragile, and expensive to make and repair, often employing expensive materials (e.g., laser cut nitinol hypotubes) and complex designs (e.g., riveted rings). Many conventional designs have a relatively high rate of failure and tend to fail catastrophically.

Catheter designs, by contrast, have relatively simple constructions. Their circular inner diameters are usually maximized to facilitate irrigation flow and they typically do not have imaging channels or deflection wires within their inner lumen that would obstruct that flow. To maximize lumen size and flow in a circular inner diameter, conventional catheter designs often position deflection wires within the catheter walls. To minimize wall thickness and overall outer diameter size, conventional catheters often employ flat deflection wires. While a flat deflection wire may effectively move a catheter in two dimensions within a plane of motion, the wire will tend to resist movement out of that plane (i.e., in a third dimension), preventing optimal steering and potentially creating a "whipping" effect.

For both endoscopes and catheters, the smallest outer diameter is desirable (e.g., permitting smaller percutaneous incisions or because of anatomical constraints). Both generally have circular inner diameters or inner lumens.

The following are incorporated by reference in their entirety: U.S. Pat. App. Pub. Nos. 2007/0299424, 2010/0056868, 2010/0312056, and 2013/0190561 and U.S. Pat. Nos. 3,521,620, 3,739,770, 4,543,090, 5,176,660, 5,368,564, 5,383,852, 5,472,017, 5,702,433, 5,746,696, 6,991,616, 7,037,290 7,766,821, 7,803,130, 8,123,721, 8,579,801, 8,721,826, and 8,834,356.

SUMMARY

Conventional endoscope designs are expensive, complex, and have high failure rates. And when they fail, they can fail catastrophically. There is a need for a simpler, cheaper design with rheological properties that reduces the risk of catastrophic failure.

In one form, an endoscope comprises an insertion tube connected to a handle. An endoscope insertion tube may comprise: a shaft comprising a braided alloy, the shaft having a lumen, an outer surface, an inner surface, a proximal end, and a distal end. It may further comprise: a thermoplastic laminate laminated to the at least a portion of the outer surface of the shaft, wherein the thermoplastic laminate comprises at least two sections. In some embodiments, the thermoplastic laminate may be laminated to the at least a portion of the outer surface of the braided tubular shaft. A laminated braided shaft will rarely fail catastrophically under normal operating conditions.

In some forms, the thermoplastic laminate may comprise a first section having a first durometer, a second section having a second durometer, a third section having a third durometer, and a fourth section having a fourth durometer. A durometer is a measure of the hardness of a material. This form may further comprise: wherein at least a portion of the first section may be proximate to the proximal end of the shaft and wherein the fourth section may be proximate to the distal end of the shaft. It may further comprise: wherein the second section may be between the first section and the third section and wherein the third section may be between the second section and the fourth section. It may further comprise: wherein the fourth durometer may be less than the first durometer, the second durometer, and the third durometer. It may further comprise: wherein the second durometer may be less than the first durometer and the third durometer.

In addition or alternatively, a liner may be fixed to at least a portion of the inner surface of a shaft, wherein an interior of the liner defines a non-circular inner lumen. In some forms, the liner may be laminated to the at least a portion of the outer surface of the shaft. It may further comprise: at least two gaps between the shaft and the liner, wherein the gaps define two deflection channels. In some forms, a deflection channel liner may be disposed within the gaps, in which case the interior of the deflection channel liner may define the deflection channel. In alternative forms, the gaps may not house a deflection channel liner and the deflection wires may be disposed within the gaps directly.

In addition or alternatively, some forms may comprise at least two deflection wires, each having a proximal end and a distal end, wherein one deflection wire may be positioned in each of at least two deflection channels. For example, in some forms, the deflection wires may be positioned within the lumen of the shaft, but not the walls of the insertion tube shaft or plastic housing.

In addition or alternatively, a working channel may be positioned within the inner lumen. Further, at least two optics channels may be positioned within the inner lumen. At least one light source may be positioned within an optics channel and proximate to the distal end of the endoscope insertion tube. At least one image sensor may be positioned within an optics channel and proximate to the distal end of the endoscope insertion tube. In some forms, the image sensor may be an image bundle and/or an analog sensor. In addition or alternative forms, the image sensor may produce a digital signal. Further, a cap may be attached to the distal end of at least two deflection wires.

In addition or alternatively, the deflection wires may have a round cross-section within middle and distal sections of an insertion tube. Whereas a flat wire may have a significantly different moment of inertia within their plane of articulation versus outside that plane, round wires do not. Flat wires' resistance to movement outside their plane of articulation can be felt by the user while the device is deflected, creating a "whipping" effect as the insertion tube is re-aligned with the wire's plane of articulation. This can be a problem in urology where the physician holds the endoscope vertically and bends the distal end of the insertion tube roughly 90 degrees into the patient. For example, if the kidney is in the horizontal plane, the endoscope insertion tube may deflect where the moment of inertia is greatest and could create unwanted force feedback when applying torque to the handle to rotate the insertion tube. Nonetheless, in addition or alternatively, one or more deflection wire may have a cross-section that may be round, oval, flat, rectangular, or other suitable shape. Deflection wires may comprise braided or solid materials, such as metal, carbon fiber, synthetic fibers, such as Kevlar®, or other tensile materials.

Such "whipping" effect may be further reduced by employing a shaft of braided material. In some forms, a shaft may comprise steel. In addition or alternatively, the shaft may comprise nitinol. In one embodiment, the shaft does not comprise nitinol because of its high cost. Nonetheless, other embodiments may have a shaft comprising nitinol.

In some forms, an endoscope may comprise a marker comprising a radio opaque material, and the marker may be positioned proximate to the cap. In addition or alternatively, the thermoplastic laminate may comprise $BaSO_4$ or other radio-opaque material, which may render the all or part of the insertion tube visible under fluoroscopy.

In addition or alternatively, the first section of the thermoplastic laminate may have a first outer diameter and the fourth section of the thermoplastic laminate may have a fourth outer diameter and wherein the fourth outer diameter may be less than the first outer diameter. In some forms, the deflection channels are not in fluid communication with the lumen. In alternative forms, the deflection channels may be in fluid communication with the lumen.

In addition or alternatively, the cap may be fixedly attached to the distal end of the shaft, the optics channels, and the working channel. In addition or alternatively, the cap may be fixedly attached to the deflection wires. In one form, the wires may be attached by welding or other suitably secure means.

In addition or alternatively, an endoscope insertion tube may comprise a preferentially bendable portion proximate to a distal end of the endoscope insertion tube. The preferentially bendable portion may comprise a shaft having an outer surface, an inner surface, and a distal end. It may further comprise: at least three thermoplastic laminate sections bonded to the at least a portion of the outer surface of the shaft, wherein the thermoplastic laminate sections are a lower durometer section, a medium durometer section, and higher durometer section. It may further comprise: wherein the lower durometer section may be bonded proximate to the distal end of the shaft and the lower durometer section may have a durometer less than a durometer of the medium durometer section and a durometer of the higher durometer section. It may further comprise: wherein the higher durometer section may be between the lower durometer section and the medium durometer section and the higher durometer section may have a durometer greater than a durometer of the lower durometer section and a durometer of the medium durometer section.

In addition or alternative, when the preferentially bendable portion is fully articulated, the angle between a first section and a third section may about 150-178 degrees or more preferably about 160-170 degrees (e.g., a middle second section may be deflection about 10-20 degrees from a neutral position). The angle between the third section and a fully deflected fourth section may be about 250 degrees or more or more preferably about 300 or more degrees.

In addition or alternatively, the endoscope insertion tube may comprise a liner bonded to at least a portion of the inner surface of the shaft, wherein an interior of the liner defines a lumen. It may further comprise: at least one gap between the shaft and the liner, wherein at least a portion of the gap defines a deflection channel. It may further comprise: at least one deflection wire positioned in the deflection channel.

In addition or alternatively, an endoscope insertion tube may comprise a shaft having an outer surface and an inner surface. It may further comprise: a liner bonded to at least a portion of the inner surface of the shaft, wherein an interior of the liner defines an inner lumen. It may further comprise: at least one gap between the shaft and the liner, wherein the gap defines a deflection channel.

In addition or alternatively, the endoscope insertion tube may comprise at least one deflection wire positioned in the deflection channel. In one embodiment, an endoscope insertion tube may comprise only one deflection wire to maximize space within the lumen. In alternative embodiments, an endoscope insertion tube may comprise, three, four, or more deflection wires to provide additional steering capabilities. In some forms, by placing deflection wires and/or deflection channels within the inner lumen of the shaft, the walls of the endoscope insertion tube can be made substantially thinner (about 0.2 mm) than many conventional catheter designs (about 0.4 mm or greater) in which the deflection wires are positioned in the catheter walls.

In some forms, an endoscope insertion tube may comprise a lower durometer section bonded proximate to a distal end of the shaft, wherein the lower durometer section may have a durometer less than a durometer of a medium durometer section and a durometer of a higher durometer section. It may further comprise: wherein the higher durometer section may be between the lower durometer section and the medium durometer section and the higher durometer section may have a durometer greater than a durometer of the lower durometer section and a durometer of the medium durometer section.

In addition or alternatively, an endoscope insertion tube may comprise a fourth thermoplastic laminate section, wherein at least a portion of the fourth thermoplastic laminate section may be proximate to a proximal end of the shaft, wherein the fourth thermoplastic laminate section may have a durometer greater than the lower durometer section and the medium durometer section.

In addition or alternatively, an endoscope insertion tube may comprise a second gap between the shaft and the liner, wherein the second gap defines a second deflection channel, and a second deflection wire positioned in the second deflection channel.

In addition or alternatively, an endoscope insertion tube may comprise a cap attached to the distal end of at least one deflection wire.

In addition or alternatively, an endoscope insertion tube may comprise a marker comprising a radio opaque material, the marker positioned proximate to the cap.

In addition or alternatively, an endoscope insertion tube may comprise a working channel and at least two optical bundles positioned within the lumen.

In another form, a method of making an endoscope insertion tube may comprise positioning a first liner over a first mandrel, wherein the first mandrel may have at least a first slot parallel to a longitudinal axis of the mandrel. It may further comprise: positioning a second liner over a second mandrel, wherein the second mandrel may be sized to fit at least partially within the first slot of the first mandrel. It may further comprise: positioning the second mandrel and the second liner at least partially within the first slot of the first mandrel.

In addition or alternatively, the method may comprise braiding a shaft around the first liner and the second liner, wherein the second liner may be between at least a portion of an inner surface of the shaft and an unbonded portion of the first liner. In addition or alternatively, a flexible shaft may be positioned around the first liner and the second liner.

In addition or alternatively, the method may comprise positioning a second mandrel at least partially within the slot and between the liner and the shaft. It may further comprise: positioning a third mandrel at least partially within the second slot and between the liner and the shaft. It may further comprise: positioning the shaft into at least two thermoplastic laminate sections having different sized outer diameters.

In addition or alternatively, the method may further comprise: positioning the shaft into at least two thermoplastic laminate sections having different durometers. It may further comprise: positioning the shaft into a first thermoplastic laminate section having a first durometer, a second thermoplastic laminate section having a second durometer, a third thermoplastic laminate section having a third durometer, and a fourth thermoplastic laminate section having a fourth durometer. It may further comprise: wherein the fourth durometer may be less than the first durometer, the second durometer, and the third durometer. It may further comprise: wherein the second durometer may be less than the first durometer and the third durometer.

The method may further comprise heating at least the first mandrel, the first liner, the second mandrel, the second liner, and the shaft. It may further comprise: fixing a bonded portion of the first liner to at least a portion of an inner surface of the shaft, but wherein no unbonded portion bonds to the inner surface of the shaft.

The method may further comprise removing the first mandrel and the second mandrel. In some forms, a mandrel may be coated with a thermoplastic with a melting point greater than the thermoplastic fusion bonding temperature of the plastic housing of the endoscope insertion tube. For example, a primary mandrel may be coated in PTFE and the plastic housing may comprise Pebax®. Such coated mandrels may be removed from the shaft and reused. In addition or alternatively, a mandrel may comprise a silver-plated copper rod. For example, a secondary mandrel may be a silver-plated copper rod and be removed by applying tension to the secondary mandrel, elongating the mandrel and thereby reducing its width, and removing it from the shaft.

In addition or alternatively, the method may comprise inserting a deflection wire within a deflection channel liner. In addition or alternatively, the method may comprise inserting a deflection wire between the shaft and the first unbonded portion of the liner, without a deflection channel liner.

In some forms, a mandrel may have a slot. In addition or alternatively, a first or second unbonded portion of the liner may be positioned proximate to a base of the slot of the mandrel, wherein the unbonded portion may not bond to the inner surface of the shaft. In addition or alternatively, a first slot and a second slot may be positioned on opposing sides of the mandrel and further comprising inserting a second deflection wire between the shaft and the second unbonded portion of the liner. In some forms, the mandrel may have four slots and the liner may have four unbonded portions.

In addition or alternatively, a mandrel for molding a liner within an insertion tube may comprise a substantially cylindrical mandrel with two lateral oval shaped slots. The mandrel may be positioned within a liner. The mandrel may have one, two, three, or four slots.

Several exemplary embodiments are described as follows.

Embodiment 1: An endoscope insertion tube comprising:
a. a braided tubular shaft, the shaft having an outer surface, an inner surface, a proximal end, a distal end, and a lumen;
b. a shaft liner comprising at least two bonded sections and at least two unbonded sections, wherein at least two bonded sections are fixedly attached to at least a portion of the inner surface of the shaft;
c. at least two gaps, wherein one gap is between the shaft and each of at least two unbonded sections of the shaft liner;
d. wherein an interior of the shaft liner defines a non-circular inner lumen;
e. at least two deflection channel liners, wherein one deflection channel liner is positioned in each of at least two gaps, and wherein an interior of each deflection channel liner defines a deflection channel;
f. at least two deflection wires, each having a proximal end and a distal end, wherein at least a portion of the at least two deflection wires are positioned in each of at least two deflection channels;
g. wherein at least a portion of at least two deflection wires are positioned within the lumen of the shaft and exterior to the inner lumen of the shaft liner;
h. a working channel positioned within the inner lumen;
i. at least two optics channels positioned within the inner lumen proximate to the distal end of the shaft;
a. at least a portion of at least one light source positioned within an optics channel and proximate to the distal end of the endoscope insertion tube;
j. at least a portion of at least one image sensor positioned within an optics channel and proximate to the distal end of the endoscope insertion tube;
k. a cap attached to the distal end of at least two deflection wires;
l. a thermoplastic laminate laminated to at least a portion of the outer surface of the shaft, the thermoplastic laminate comprising:
  i. a first section having at least a first durometer,
  ii. a second section having at least a second durometer,
  iii. a third section having at least a third durometer, and
  iv. a fourth section having at least a fourth durometer,
m. wherein at least a portion of the first section is proximate to the proximal end of the shaft and wherein at least a portion of the fourth section is proximate to the distal end of the shaft;
n. wherein the fourth section is distal to the third section and the third section is distal to the second section;
o. wherein the fourth durometer is less than the first durometer, the second durometer, and the third durometer; and
p. wherein the second durometer is less than the first durometer and the third durometer.

Embodiment 2: An endoscope insertion tube comprising:
a. a shaft having an outer surface, an inner surface, a proximal end, a distal end, and a lumen;
b. a plastic housing fixed to at least a portion of the outer surface of the shaft;
c. at least one deflection wire, wherein at least a portion of the deflection wire is within the lumen of the shaft;
d. a light source, wherein at least a portion of the light source is positioned within the lumen of the shaft; and
e. an image sensor, wherein at least a portion of the image sensor is positioned within the lumen of the shaft.

Embodiment 3: An endoscope insertion tube comprising:
a. a shaft having an outer surface, an inner surface, a proximal end, a distal end, and a lumen;

b. a plastic housing fixed to at least a portion of the outer surface of the shaft;

c. a first liner comprising at least one first portion and at least one second portion, wherein the first portion is fixed to at least a portion of the inner surface of the shaft and the second portion is not fixed to the inner surface of the shaft;

d. at least one gap between the shaft and the second portion of the first liner.

Embodiment 4: An endoscope insertion tube comprising a preferentially bendable portion proximate to a distal end of the endoscope insertion tube, the preferentially bendable portion comprising:

a. a shaft having an outer surface, an inner surface, a proximal end, a distal end, and a lumen;

b. a lower durometer plastic laminate section laminated to at least a portion of the outer surface of the shaft proximate to the distal end of the shaft;

c. a higher durometer plastic laminate section laminated to at least a portion of the outer surface of the shaft, wherein the lower durometer plastic laminate section is distal to the higher durometer plastic laminate section;

d. a medium durometer plastic laminate section laminated to at least a portion of the outer surface of the shaft, wherein the higher durometer plastic laminate section is distal to the medium durometer plastic laminate section;

e. wherein the lower durometer section has a durometer less than a durometer of the medium durometer plastic laminate section and a durometer of the higher durometer plastic laminate section.

Embodiment 5: The endoscope insertion tube directed to embodiment 3, further comprising:

a. at least one deflection wire, wherein at least a portion of the deflection wire is within the lumen of the shaft;

b. a light source, wherein at least a portion of the light source is positioned within the lumen of the shaft; and c. an image sensor, wherein at least a portion of the image sensor is positioned within the lumen of the shaft.

Embodiment 6: The endoscope insertion tube directed to embodiment 4, further comprising:

a. at least one deflection wire, wherein at least a portion of the deflection wire is within the lumen of the shaft;

b. a light source, wherein at least a portion of the light source is positioned within the lumen of the shaft; and c. an image sensor, wherein at least a portion of the image sensor is positioned within the lumen of the shaft.

Embodiment 7: The endoscope insertion tube directed to embodiment 2, further comprising:

a. a first liner comprising a first portion and a second portion, wherein the first portion is fixed to at least a portion of the inner surface of the shaft and the second portion is not fixed to the inner surface of the shaft;

b. at least one gap between the shaft and the second portion of the first liner.

Embodiment 8: The endoscope insertion tube directed to embodiment 4, further comprising:

a. a first liner comprising a first portion and a second portion, wherein the first portion is fixed to at least a portion of the inner surface of the shaft and the second portion is not fixed to the inner surface of the shaft;

b. at least one gap between the shaft and the second portion of the first liner.

Embodiment 9: The endoscope insertion tube directed to embodiment 2, wherein the plastic housing comprises:

a. a lower durometer section laminated to at least a portion of the outer surface of the shaft proximate to the distal end of the shaft;

b. a higher durometer section laminated to at least a portion of the outer surface of the shaft, wherein the lower durometer section is distal to the higher durometer section;

c. a medium durometer section laminated to at least a portion of the outer surface of the shaft, wherein the higher durometer section is distal to the medium durometer section;

d. wherein the lower durometer section has a durometer less than a durometer of the medium durometer section and a durometer of the higher durometer section.

Embodiment 10: The endoscope insertion tube directed to embodiment 3, wherein the plastic housing comprises:

a. a lower durometer section laminated to at least a portion of the outer surface of the shaft proximate to the distal end of the shaft;

b. a higher durometer section laminated to at least a portion of the outer surface of the shaft, wherein the lower durometer section is distal to the higher durometer section;

c. a medium durometer section laminated to at least a portion of the outer surface of the shaft, wherein the higher durometer section is distal to the medium durometer section;

d. wherein the lower durometer section has a durometer less than a durometer of the medium durometer section and a durometer of the higher durometer section.

Embodiment 11: The endoscope insertion tube directed to of any of embodiments 2, 7, or 9, wherein the deflection wire comprises braided steel.

Embodiment 12: The endoscope insertion tube directed to of any of embodiments 2, 7, or 9, wherein the deflection wire comprises solid core steel.

Embodiment 13: The endoscope insertion tube directed to of any of embodiments 2, 7, or 9, comprising at least two deflection wires.

Embodiment 14: The endoscope insertion tube directed to of any of embodiments 2, 7, or 9, comprising at least four deflection wires.

Embodiment 15: The endoscope insertion tube directed to of any of embodiments 2, 7, or 9, wherein the image sensor is proximate to the distal end of the shaft.

Embodiment 16: The endoscope insertion tube directed to of any of embodiments 2, 7, or 9, wherein the light source is proximate to the distal end of the shaft.

Embodiment 17: The endoscope insertion tube directed to of any of embodiments 2, 7, or 9, further comprising a channel and at least a portion of the deflection wire positioned in the channel.

Embodiment 18: The endoscope insertion tube directed to of any of embodiments 2, 7, or 9, further comprising at least a first and second channel proximate to the distal end of the shaft and at least a portion of the light source in the first channel and at least a portion of the image sensor positioned in the second channel.

Embodiment 19: The endoscope insertion tube directed to of any of embodiments 3, 5, or 10, further comprising at least one deflection wire, wherein at least a portion of the deflection wire is positioned within the lumen of the shaft and exterior to an inner lumen of the first liner.

Embodiment 20: The endoscope insertion tube directed to of any of embodiments 3, 5, or 10, further comprising at least one deflection wire, wherein at least a portion of the deflection wire is in the gap.

Embodiment 21: The endoscope insertion tube directed to of any of embodiments 3, 5, or 10, further comprising a second liner in the gap, wherein an interior of the second liner defines a tubular deflection channel.

Embodiment 22: The endoscope insertion tube directed to embodiment 21, further comprising at least one deflection wire, wherein at least a portion of the deflection wire is in the tubular deflection channel.

Embodiment 23: The endoscope insertion tube directed to of any of embodiments 3, 5, or 10, further comprising at least two second portions of the first liner and at least two gaps between the shaft and each of the at least two second portions.

Embodiment 24: The endoscope insertion tube directed to embodiment 23, further comprising at least two deflection wires, wherein at least a portion of each deflection wire is positioned within the lumen of the shaft and exterior to an inner lumen of the first liner.

Embodiment 25: The endoscope insertion tube directed to embodiment 23, further comprising at least two deflection wires, wherein at least a portion of each deflection wire is in at least one gap.

Embodiment 26: The endoscope insertion tube directed to embodiment 23, wherein the at least two gaps are a first gap and a second gap, further comprising a second liner in the first gap and a third liner in the second gap, wherein an interior of the second liner defines a first tubular deflection channel and wherein an interior of the third liner defines a second tubular deflection channel.

Embodiment 27: The endoscope insertion tube directed to embodiment 26, further comprising at least one deflection wire, wherein at least a portion of the deflection wire is in at least one tubular deflection channel.

Embodiment 28: The endoscope insertion tube directed to embodiment 26, further comprising at least two deflection wires, wherein at least a portion of each deflection wire is in at least one tubular deflection channel.

Embodiment 29: The endoscope insertion tube directed to of any of embodiments 2-3, 5, or 7, wherein the plastic housing is cast over at least a portion of the outer surface of the shaft.

Embodiment 30: The endoscope insertion tube directed to of any of embodiments 2-3, 5, 7, or 9-10, wherein the plastic housing is fixed to at least a portion of the outer surface of the shaft by lamination.

Embodiment 31: The endoscope insertion tube directed to of any of embodiments 2-3, 5, 7, or 9-10, wherein the plastic housing comprises thermoplastic.

Embodiment 32: The endoscope insertion tube directed to of any of embodiments 2-3, 5, 7, or 9-10, wherein the plastic housing comprises at least one plastic laminate section.

Embodiment 33: The endoscope insertion tube directed to of any of embodiments 2-3, 5, 7, or 9-10, wherein the plastic housing comprises at least a first plastic laminate section and a second plastic laminate section, wherein the first plastic laminate section has a durometer that is different than a durometer of the second plastic laminate section.

Embodiment 34: The endoscope insertion tube directed to of any of embodiments 2-3, 5, 7, or 9-10, wherein the plastic housing comprises at least a first plastic laminate section, a second plastic laminate section, and a third plastic laminate section, and wherein the first plastic laminate section has a durometer that is different than a durometer of the second plastic laminate section and a durometer of the second plastic laminate section.

Embodiment 35: The endoscope insertion tube directed to embodiment 34, wherein the durometer of the second plastic laminate section is different than the durometer of the third plastic laminate section.

Embodiment 36: The endoscope insertion tube directed to embodiment 34, wherein the durometer of the second plastic laminate section is substantially equal to the durometer of the third plastic laminate section.

Embodiment 37: The endoscope insertion tube directed to embodiment 34, wherein the first plastic laminate section is distal to the second and third plastic laminate sections.

Embodiment 38: The endoscope insertion tube directed to embodiment 34, wherein the second plastic laminate section is distal to the first and third plastic laminate sections.

Embodiment 39: The endoscope insertion tube directed to embodiment 34, wherein the third plastic laminate section is distal to the first and second plastic laminate sections.

Embodiment 40: The endoscope insertion tube directed to of any of embodiments 2-3, 5, 7, or 9-10, wherein the plastic housing comprises at least a first section and a second section, wherein an outer diameter of the first section is different than an outer diameter of the second section.

Embodiment 41: The endoscope insertion tube directed to embodiment 40, wherein the second section is distal to the first section and the outer diameter of the second section is less than the outer diameter of the first section.

Embodiment 42: The endoscope insertion tube directed to of any of embodiments 2-3, 5, 7, or 9-10, wherein the plastic housing comprises a radio opaque material.

Embodiment 43: The endoscope insertion tube directed to of any of embodiments 2-3, 5, 7, or 9-10, further comprising at least one deflection channel positioned within the lumen of the shaft.

Embodiment 44: The endoscope insertion tube directed to embodiment 45, wherein the deflection channel is not in fluid communication with the lumen of the shaft.

Embodiment 45: The endoscope insertion tube directed to of any of embodiments 3, 5, or 10, wherein at least a portion of the gap defines a deflection channel.

Embodiment 46: The endoscope insertion tube directed to embodiment 45, further comprising a second gap between the shaft and the first liner, wherein the second gap defines a second deflection channel.

Embodiment 47: The endoscope insertion tube directed to embodiment 45, wherein the deflection channel is not in fluid communication with the lumen of the shaft.

Embodiment 48: The endoscope insertion tube directed to of any of embodiments 4, 6, or 8, wherein an outer diameter of the medium durometer plastic laminate section is greater than an outer diameter of the lower durometer plastic laminate section.

Embodiment 49: The endoscope insertion tube directed to of any of embodiments 4, 6, or 8, further comprising a fourth plastic laminate section, wherein at least a portion of the fourth thermoplastic laminate section is proximate to a proximal end of the shaft, wherein the fourth thermoplastic laminate section has a durometer greater than the lower durometer plastic laminate section and the medium durometer plastic laminate section.

Embodiment 50: The endoscope insertion tube directed to embodiment 49, wherein the lower durometer plastic laminate section has an outer diameter that is less than an outer diameter of the fourth plastic laminate section.

Embodiment 51: The endoscope insertion tube directed to of any of embodiments 4, 6, or 8, wherein one or more plastic laminate sections comprise a radio opaque material.

Embodiment 52: The endoscope insertion tube directed to of any of embodiments 2-10, wherein the shaft comprises a metal alloy.

Embodiment 53: The endoscope insertion tube directed to of any of embodiments 2-10, wherein the shaft comprises steel.

Embodiment 54: The endoscope insertion tube directed to of any of embodiments 2-10, further comprising a working channel positioned with the lumen of the shaft.

Embodiment 55: The endoscope insertion tube directed to of any of embodiments 2-10, further comprising a cap attached to the distal end of the shaft.

Embodiment 56: The endoscope insertion tube directed to of any of embodiments 2, 7, or 9, further comprising a cap attached to a distal end of the at least one deflection wire.

Embodiment 57: The endoscope insertion tube directed to of any of embodiments 2, 7, or 9, further comprising a second deflection wire and a cap attached to a distal end of at least two deflection wires.

Embodiment 58: The endoscope insertion tube directed to of any of embodiments 2-10, further comprising a radio opaque marker attached proximate to the distal end of the shaft.

Embodiment 59: The endoscope insertion tube directed to of any of embodiments 3, 5, or 10, further comprising at least four gaps and at least four tubular deflection channel liners positioned within the gaps.

Embodiment 60: The endoscope insertion tube directed to of any of embodiments 2-3, 5, 7, or 9-10, wherein the plastic housing comprises at least a first section and a second section, wherein an end of the first section at least partially overlaps an end of the second section.

Embodiment 61: An assembly for making an endoscope insertion tube or components thereof, the assembly comprising:
  a. a primary mandrel having a non-circular perimeter, a first slot, wherein the first slot has a depth at a first section of the primary mandrel, a longitudinal axis, a width at the first section that is a minimum distance across a plane perpendicular to the longitudinal axis, wherein the plane substantially bisects the primary mandrel and intersects the slot, and a height at the first section that is perpendicular to the width;
  b. a first mandrel having a width; and
  c. at least a portion of the first secondary mandrel positioned within the first slot of the primary mandrel.

Embodiment 62: The assembly directed to embodiment 61, further comprising a second secondary mandrel having a width and wherein the primary mandrel has a second slot and at least a portion of the second mandrel is positioned within the second slot of the primary mandrel.

Embodiment 63: The assembly directed to embodiment 61, further comprising at least four mandrels and wherein the primary mandrel has at least four slots and at least a portion of each of at least four mandrels are positioned within at least one slot of the primary mandrel.

Embodiment 64: The assembly directed to embodiment 61, wherein the first mandrel is proximate to a base of the first slot.

Embodiment 65: The assembly directed to embodiment 61, further comprising a first liner positioned around the first mandrel.

Embodiment 66: The assembly directed to embodiment 65, wherein the first liner is tubular.

Embodiment 67: The assembly directed to embodiment 62, further comprising a first liner positioned around the first mandrel and a second liner positioned around the second mandrel.

Embodiment 68: The assembly directed to embodiment 62, further comprising a second liner positioned around the second mandrel.

Embodiment 69: The assembly directed to of any of embodiments 61-68, further comprising a shaft liner positioned around the primary mandrel and between the primary mandrel and the first mandrel.

Embodiment 70: The assembly directed to of any of embodiments 62-63, further comprising a shaft liner positioned around the primary mandrel and between the primary mandrel and at least two mandrels.

Embodiment 71: The assembly directed to embodiment 61, further comprising:
  a. a shaft liner positioned around the primary mandrel; and
  b. a first liner positioned around the first mandrel;
  c. wherein the shaft liner and the first liner are between the primary mandrel and the first mandrel.

Embodiment 72: The assembly directed to embodiment 62, further comprising:
  a. a shaft liner positioned around the primary mandrel; and
  b. at least two deflection channel liners positioned around at least two mandrels.

Embodiment 73: The assembly directed to embodiment 63, further comprising:
  a. a shaft liner positioned around the primary mandrel; and
  b. at least two deflection channel liners positioned around at least two mandrels.

Embodiment 74: The assembly directed to embodiment 61, further comprising a shaft positioned around at least a portion of the primary mandrel and at least a portion of the first mandrel.

Embodiment 75: The assembly directed to embodiment 71, further comprising a shaft positioned around at least a portion of the shaft liner and at least a portion of the first liner.

Embodiment 76: The assembly directed to embodiment 71, further comprising a shaft of braided metal, wherein the metal is braided around at least a portion of the shaft liner and at least a portion of the first liner.

Embodiment 77: The assembly directed to embodiment 72, further comprising a shaft positioned around at least a portion of the shaft liner and at least a portion of at least two deflection channel liners.

Embodiment 78: The assembly directed to embodiment 73, further comprising a shaft positioned around at least a portion of the shaft liner and at least a portion of at least two deflection channel liners.

Embodiment 79: The assembly directed to embodiment 72, further comprising a shaft of braided metal, wherein the metal is braided around at least a portion of the shaft liner and at least a portion of at least two deflection channel liners.

Embodiment 80: The assembly directed to embodiment 73, further comprising a shaft of braided metal, wherein the metal is braided around at least a portion of the shaft liner and at least a portion of at least two deflection channel liners.

Embodiment 81: The assembly directed to of any of embodiments 74-80, further comprising a plastic housing positioned around at least a portion of the shaft.

Embodiment 82: The assembly directed to embodiment 81, wherein the plastic housing comprises:
  a. a lower durometer section laminated to at least a portion of an outer surface of the shaft proximate to a distal end of the shaft;
  b. a higher durometer section laminated to at least a portion of the outer surface of the shaft, wherein the lower durometer section is distal to the higher durometer section;
  c. a medium durometer section laminated to at least a portion of the outer surface of the shaft, wherein the higher durometer section is distal to the medium durometer section;

d. wherein the lower durometer section has a durometer less than a durometer of the medium durometer section and a durometer of the higher durometer section.

Embodiment 83: The assembly directed to embodiment 81, wherein the plastic housing is cast over at least a portion of the outer surface of the shaft.

Embodiment 84: The assembly directed to embodiment 81, wherein the plastic housing is fixed to at least a portion of the outer surface of the shaft by lamination.

Embodiment 85: The assembly directed to embodiment 81, wherein the plastic housing comprises thermoplastic.

Embodiment 86: The assembly directed to embodiment 81, wherein the plastic housing comprises at least one plastic laminate section.

Embodiment 87: The assembly directed to embodiment 81, wherein the plastic housing comprises at least a first plastic laminate section and a second plastic laminate section, wherein the first plastic laminate section has a durometer that is different than a durometer of the second plastic laminate section.

Embodiment 88: The assembly directed to embodiment 81, wherein the plastic housing comprises at least a first plastic laminate section, a second plastic laminate section, and a third plastic laminate section, and wherein the first plastic laminate section has a durometer that is different than a durometer of the second plastic laminate section and a durometer of the second plastic laminate section.

Embodiment 89: The assembly directed to embodiment 88, wherein the durometer of the second plastic laminate section is different than the durometer of the third plastic laminate section.

Embodiment 90: The assembly directed to embodiment 88, wherein the durometer of the second plastic laminate section is substantially equal to the durometer of the third plastic laminate section.

Embodiment 91: The assembly directed to embodiment 88, wherein the first plastic laminate section is distal to the second and third plastic laminate sections.

Embodiment 92: The assembly directed to embodiment 88, wherein the second plastic laminate section is distal to the first and third plastic laminate sections.

Embodiment 93: The assembly directed to embodiment 88, wherein the third plastic laminate section is distal to the first and second plastic laminate sections.

Embodiment 94: The assembly directed to embodiment 81, wherein the plastic housing comprises at least a first section and a second section, wherein an outer width of the first section is different than an outer width of the second section.

Embodiment 95: The assembly directed to embodiment 81, wherein the second section is distal to the first section and the outer width of the second section is less than the outer width of the first section.

Embodiment 96: The assembly directed to embodiment 81, wherein the plastic housing comprises a radio opaque material.

Embodiment 97: The assembly directed to embodiment 81, wherein the plastic housing comprises at least a first section and a second section, wherein an end of the first section at least partially overlaps an end of the second section.

Embodiment 98: The assembly directed to embodiment 81, further comprising positioning a shrinkable tube around at least a portion of the plastic housing.

Embodiment 99: The assembly directed to embodiment 82, further comprising positioning a shrinkable tube around at least a portion of the plastic housing.

Embodiment 100: The assembly directed to embodiment 61, wherein the height at the first section of the primary mandrel is greater than a height at a second section of the mandrel.

Embodiment 101: The assembly directed to embodiment 100, further comprising a shaft positioned around at least a portion of the primary mandrel and at least a portion of the first mandrel and wherein the first section of the primary mandrel is proximate to a distal end of the shaft.

Embodiment 102: The assembly directed to embodiment 61, wherein the width at a first section of the primary mandrel is less than a width at a second section of the mandrel.

Embodiment 103: The assembly directed to embodiment 102, further comprising a shaft positioned around at least a portion of the primary mandrel and at least a portion of the first mandrel and wherein the first section of the primary mandrel is proximate to a distal end of the shaft.

Embodiment 104: The assembly directed to embodiment 61, wherein the depth of the first slot at the first section of the primary mandrel is greater than a depth of the first slot at a second section of the primary mandrel.

Embodiment 105: The assembly directed to embodiment 104, wherein a depth of a second slot at the first section of the primary mandrel is greater than a depth of the second slot at the second section of the primary mandrel.

Embodiment 106: The assembly directed to embodiment 105, wherein the depth of the first slot at the first section of the primary mandrel is substantially equal to the depth of the second slot at the first section of the primary mandrel.

Embodiment 107: The assembly directed to embodiment 105, wherein the depth of the first slot at the second section of the primary mandrel is substantially equal to the depth of the second slot at the second section of the primary mandrel.

Embodiment 108: The assembly directed to embodiment 104, further comprising a shaft positioned around at least a portion of the primary mandrel and at least a portion of the first mandrel and wherein the first section of the primary mandrel is proximate to a proximal end of the shaft and the second section of the primary mandrel is proximate to a distal end of the shaft.

Embodiment 109: The assembly directed to embodiment 105, further comprising a shaft positioned around at least a portion of the primary mandrel and at least a portion of the first mandrel and wherein the first section of the primary mandrel is proximate to a proximal end of the shaft and the second section of the primary mandrel is proximate to a distal end of the shaft.

Embodiment 110: The assembly directed to embodiment 61, wherein the width of the first mandrel is less than or equal to the depth of the first slot.

Embodiment 111: The assembly directed to embodiment 61, wherein the width of the first mandrel is greater than the depth of the first slot.

Embodiment 112: The assembly directed to embodiment 62, wherein the width of the first mandrel is approximately equal to the width of the second mandrel.

Embodiment 113: The assembly directed to embodiment 61, wherein the width of the first section of the primary mandrel is at least three times greater than the width of the first mandrel.

Embodiment 114: The assembly directed to embodiment 61, wherein the width of the first section of the primary mandrel is at least five times greater than the width of the first mandrel.

Embodiment 115: The assembly directed to embodiment 61, wherein the width of the first section of the primary mandrel is less than three times the width of the first mandrel.

Embodiment 116: The assembly directed to embodiment 61, wherein the width of the first section of the primary mandrel is less than twice width of the first mandrel.

Embodiment 117: The assembly directed to embodiment 61, wherein the height of the first section of the primary mandrel is at least three times greater than the width of the first mandrel.

Embodiment 118: The assembly directed to embodiment 61, wherein the height of the first section of the primary mandrel is at least six times greater than the width of the first mandrel.

Embodiment 119: The assembly directed to embodiment 61, wherein the height of the first section of the primary mandrel is less than twice than the width of the first mandrel.

Embodiment 120: The assembly directed to embodiment 61, wherein the height of the first section of the primary mandrel is less than three times greater than the width of the first mandrel.

Embodiment 121: A method of making an endoscope insertion tube or components thereof, the method comprising: positioning at least a portion of a first mandrel within a first slot of a primary mandrel.

Embodiment 122: The method directed to embodiment 121, further comprising positioning at least a portion of a second mandrel within a second slot of the primary mandrel.

Embodiment 123: The method directed to embodiment 121, further comprising positioning at least a portion of each of at least four mandrels within each of at least four slots of the primary mandrel.

Embodiment 124: The method directed to embodiment 121, further comprising positioning a shaft liner around the primary mandrel, wherein the shaft liner is between the primary mandrel and the first mandrel.

Embodiment 125: The method directed to embodiment 121, further comprising:
 a. positioning a shaft liner around the primary mandrel;
 b. positioning a first deflection channel liner around the first mandrel;
 c. positioning a second deflection channel liner around a second mandrel; and
 d. positioning at least a portion of the second mandrel within a second slot of the primary mandrel.

Embodiment 126: The method directed to embodiment 121, further comprising: braiding a shaft around at least a portion of the primary mandrel and the first mandrel.

Embodiment 127: The method directed to embodiment 125, further comprising: braiding a shaft around at least a portion of the shaft liner, the first deflection channel liner, and the second deflection channel liner.

Embodiment 128: The method directed to embodiment 121, further comprising: positioning a shaft around at least a portion of the primary mandrel and the first mandrel.

Embodiment 129: The method directed to embodiment 125, further comprising: positioning a shaft around at least a portion of the shaft liner, the first deflection channel liner, and the second deflection channel liner.

Embodiment 130: The method directed to embodiment 126, further comprising: positioning a plastic housing around at least a portion of the shaft.

Embodiment 131: The method directed to embodiment 127, further comprising: positioning a plastic housing around at least a portion of the shaft.

Embodiment 132: The method directed to embodiment 130, wherein the plastic housing comprises thermoplastic.

Embodiment 133: The method directed to embodiment 131, wherein the plastic housing comprises thermoplastic.

Embodiment 134: The method directed to embodiment 130, further comprising:
 positioning a shrinkable tube around at least a portion of the plastic housing.

Embodiment 135: The method directed to embodiment 131, further comprising: positioning a shrinkable tube around at least a portion of the plastic housing.

Embodiment 136: The method directed to of any of embodiments 126-135, further comprising: laminating at least two thermoplastic sections around at least a portion of the shaft.

Embodiment 137: The method directed to of any of embodiments 126-135, further comprising: heating at least two thermoplastic sections around at least a portion of the shaft.

Embodiment 138: The method directed to embodiment 136, wherein an end of a first thermoplastic section at least partially overlaps an end of a second thermoplastic section.

Embodiment 139: The method directed to embodiment 137, wherein an end of a first thermoplastic section at least partially overlaps an end of a second thermoplastic section.

Embodiment 140: The method directed to embodiment 130, further comprising: compressing the plastic housing.

Embodiment 141: The method directed to embodiment 131, further comprising:
 compressing the plastic housing.

Embodiment 142: The method directed to embodiment 126, further comprising: fixing at least a portion of the shaft liner to the shaft.

Embodiment 143: The method directed to embodiment 127, further comprising: fixing at least a portion of the shaft liner to the shaft.

Embodiment 144: The method directed to embodiment 142, further comprising: forming a gap between at least a first portion of the shaft liner and the shaft.

Embodiment 145: The method directed to embodiment 144, further comprising: inserting a deflection wire within the gap.

Embodiment 146: The method directed to embodiment 143, further comprising: forming a gap between at least a first portion of the shaft liner and the shaft, wherein the first deflection channel liner is positioned within the gap.

Embodiment 147: The method directed to embodiment 146, further comprising: inserting a deflection wire within the deflection channel liner.

Embodiment 148: The method directed to embodiment 124, further comprising: removing the primary mandrel from the shaft liner.

Embodiment 149: The method directed to embodiment 125, further comprising:
 a. removing the primary mandrel from the shaft liner;
 b. removing the first mandrel from the first deflection channel liner; and
 c. removing the second mandrel from the second deflection channel liner.

Embodiment 150: The method of either directed to embodiments 124 or 125, further comprising: positioning at least a working channel within an inner lumen of the shaft liner.

Embodiment 151: The method of either directed to embodiments 124 or 125, further comprising: positioning at least a two optics channels within an inner lumen of the shaft liner.

Embodiment 152: The method of either directed to embodiments 124 or 125, further comprising: positioning at least a portion of at least one light source within an optics channel and proximate to a distal end of the shaft.

Embodiment 153: The method of either directed to embodiments 124 or 125, further comprising: positioning at least a portion of at least one image sensor within an optics channel and proximate to a distal end of the shaft.

Embodiment 154: The method of either directed to embodiments 124 or 125, further comprising: attaching a cap to a distal end of the shaft.

Embodiment 155: The method of either directed to embodiments 145 or 147, further comprising: welding a cap to a distal end of at least one deflection wire.

Embodiment 156: The method directed to embodiment 126, further comprising: casting a plastic housing over at least a portion of the outer surface of the shaft.

Embodiment 157: The method directed to embodiment 127, further comprising:

casting a plastic housing over at least a portion of the outer surface of the shaft.

Embodiment 158: A method of making an endoscope insertion tube or components thereof, the method comprising:

a. providing an assembly directed to of any of embodiments 61-68; and b. positioning at least a portion of the first secondary mandrel within a first slot of the primary mandrel.

Embodiment 159: A method of making an endoscope insertion tube or components thereof, the method comprising:

a. providing an assembly directed to of any of embodiments 81; and b. positioning at least a portion of the first secondary mandrel within a first slot of the primary mandrel.

Embodiment 160: A method of making an endoscope insertion tube or components thereof, the method comprising:

a. providing an assembly directed to of any of embodiments 61-120; and b. positioning at least a portion of the first secondary mandrel within a first slot of the primary mandrel.

In an additional embodiment, the product made according to any of the foregoing methods.

Many embodiments of the invention described above may provide significant advantages over conventional endoscopes. First, an endoscope insertion tube comprising a braided shaft with a laminated plastic housing may have superior kink resistance, pushability, and toque transmission, which enhance maneuverability within the anatomy.

Second, if such an endoscope insertion tube fails, it will usually fail gradually, not catastrophically, potentially allowing a physician to complete the procedure without a replacement device.

Third, if using sections with differing durometers and attaching the deflection wires directly to the cap, the embodiment allows for a smaller outer diameter at the distal end. Moreover, using the durometer configurations discussed above may provide an advantageous deflection tangent (i.e., the size of the area at least partially enclosed by a fully deflected distal end and the rest of the endoscope insertion tube), which could, for example, enhance access to the lower pole renal anatomy while avoiding kinking and/or locking the insertion tube.

Fourth, if deflection wires are positioned within lumen of a shaft, a smaller, circular outer diameter may be achieved than if the deflection wires were positioned within the shaft walls. Further, deflection wires with a circular cross-section may be used without increasing the outer diameter of the insertion tube or the thickness of the shaft walls.

The above summary is not intended to describe each illustrated embodiment or every possible implementation. These and other features, aspects, and advantages of the invention will become better understood with regard to the accompanying drawings, description, and claims.

BRIEF DESCRIPTION OF THE DRAWINGS

The accompanying figures, where like reference numerals refer to identical or functionally similar elements throughout the separate views, which are not true to scale, serve to illustrate exemplary embodiments, forms, and aspects of the invention and to explain principles and advantages thereof.

DESCRIPTION

Flexible endoscopes, components thereof, and methods of making same are described. In the interest of clarity and conciseness, not all features of an actual implementation—e.g., dimensions, tolerances, etc. —are described in this disclosure. As used in this disclosure, the terms "about" or "approximately" apply to all numeric values, whether or not explicitly indicated. These terms generally refer to a range of numbers that one of skill in the art would consider equivalent to the recited values (i.e., having the same function or result). It will be appreciated that in the development of a product or method embodying the invention, the developer must make numerous implementation-specific decisions to achieve the developer's specific goals, such as compliance with manufacturing and business-related constraints, that will vary from one implementation to another. Moreover, it will be appreciated that such a development effort may be complex and time-consuming, but would nevertheless be a routine undertaking for those of ordinary skill in the art having the benefit of this disclosure.

Figure 1A:
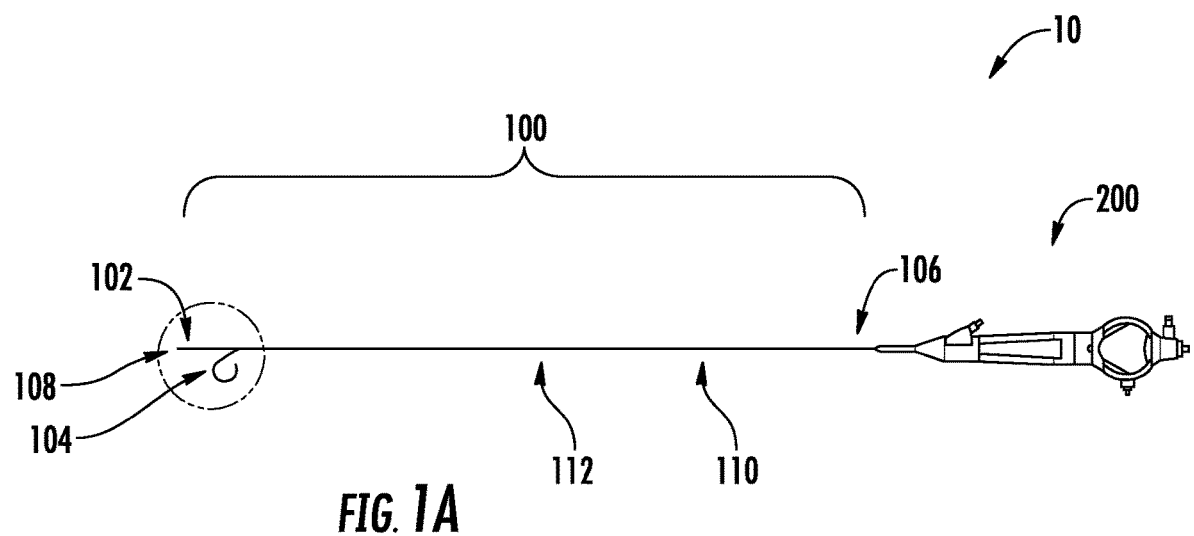
FIG. 1A is a side elevation view of an embodiment described herein.
Figure 1B:
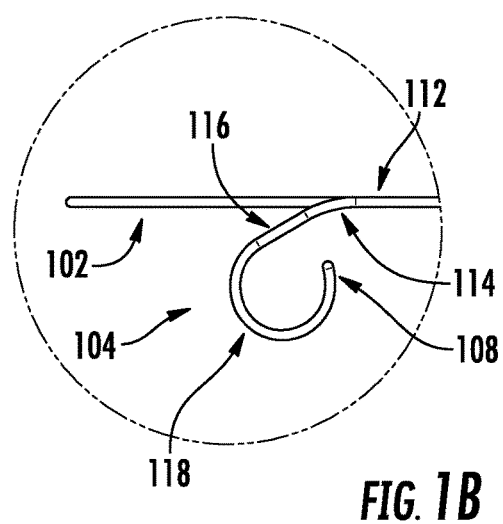
FIG. 1B is a detail view of FIG. 1A

An apparatus embodying features of the present invention is shown in FIGS. 1A and 1B. A flexible endoscope 10 comprises an endoscope insertion tube 100 connected to a handle 200. The insertion tube 100 has a distal end 108 and a proximal end 106 relative to the handle 200.

Figure 6A:
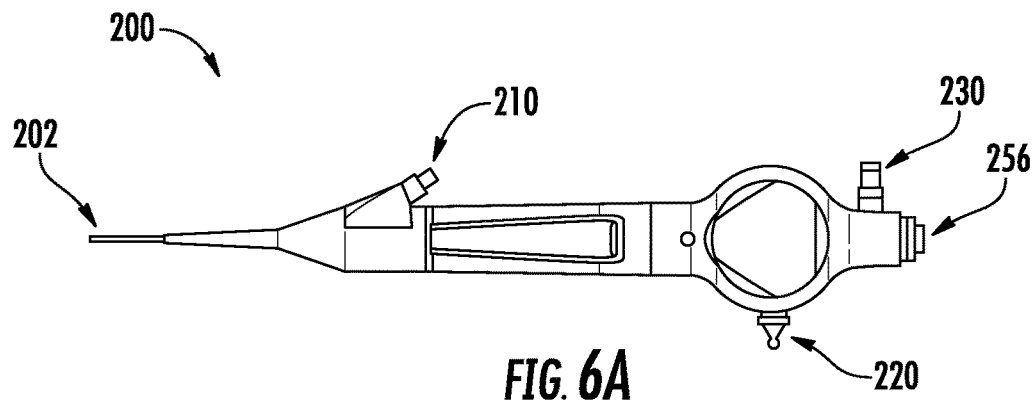
FIG. 6A is a side elevation view of a handle 200.

In one form of the invention, endoscope insertion tube 100 remains at a neutral position 102 until a user actuates a trigger 220 (see FIGS. 1A and 6A), causing the distal end 108 to deflect and assume a deflected position 104. In one plane, the angle of deflection of the distal end 108 may range from 0 degrees at the neutral position 102 to preferably plus or minus 270 or more preferably 300 or more degrees when fully deflected (i.e., in either direction), and all angles in between. In some embodiments, deflection may be in two or three dimensions. When the trigger 220 is released, the handle 200 a biasing force may return the trigger to its neutral position, moving the distal end 108 towards neutral position 102. The ability to articulate the distal end 108 of the endoscope insertion tube 100 enhances steerability.

In one form, the endoscope insertion tube 100 comprises a plastic laminate comprising four sections: (i) a relatively high durometer proximal section 112, preferably beginning at the proximal end 106 and continuing for most of the length of the endoscope insertion tube 100; (ii) an intermediate durometer middle section 114; (iii) a relatively high durometer middle section 116; and (iv) a relatively low durometer distal section 118, proximate to the distal end 108 of endoscope insertion tube 100. The specific durometer used may depend on the application, but preferred ranges for each of the sections are:

first section 112 . . . preferably about 50-140 durometers or more durometers and more preferably about 65-130 and even more preferably about 70-120 durometers;

second section 114 . . . preferably about 40-100 durometers and more preferably about 45-75 durometers and even more preferably about 50-60 durometers;

third section 116 . . . preferably about 50-140 durometers or more durometers and more preferably about 65-130 and even more preferably about 70-120 durometers;

fourth section 118 . . . preferably about 15-55 durometers or less and more preferably about 20-50 durometers and even more preferably about 30-40 durometers.

Regardless of the foregoing preferred ranges, however, the second section 114 preferably has a durometer less than the durometers of the first and third sections 112, 116 and the fourth section 118 preferably has a durometer less than the durometers of the first, second, and third sections 112, 114, 116. The durometers of the first and third sections 112, 116 may be the same or different. Further embodiments may have one, two or three sections or even five or more sections, each with the same of different durometers.

In addition or alternatively, the second section 114 may be more flexible (i.e., less rigid) than the first and third sections 112, 116 and the first, second, and third sections 112, 114, 116 may be less flexible (i.e., more rigid) than the fourth section 118. The flexibility or rigidity of the first and third sections 112, 116 may be the same or different.

In addition or alternatively, when in a deflected position 104, the second section 114 may have a smaller bend radius than the first and third sections 112, 116, and the fourth section 118 may have a smaller bend radius and shorter deflection tangent than the second section 144. The bend radius of the first and third sections 112, 116 may be the same or different.

In one embodiment, the length of the first section 112 may be about 50-70 cm, the second section 114 may be about 1-3 cm, the third section 116 may be about 1-3 cm, and the fourth section 118 may be about 4-6 cm.

In one embodiment, the laminate may be made of a plastic or a thermoplastic, such as polyether block amide (also known as Pebax®), polytetrafluoroethylene ("PTFE"), or nylon. Different sections of laminate may comprise the same or different materials as other sections, including combinations of the foregoing materials.

Figure 2:
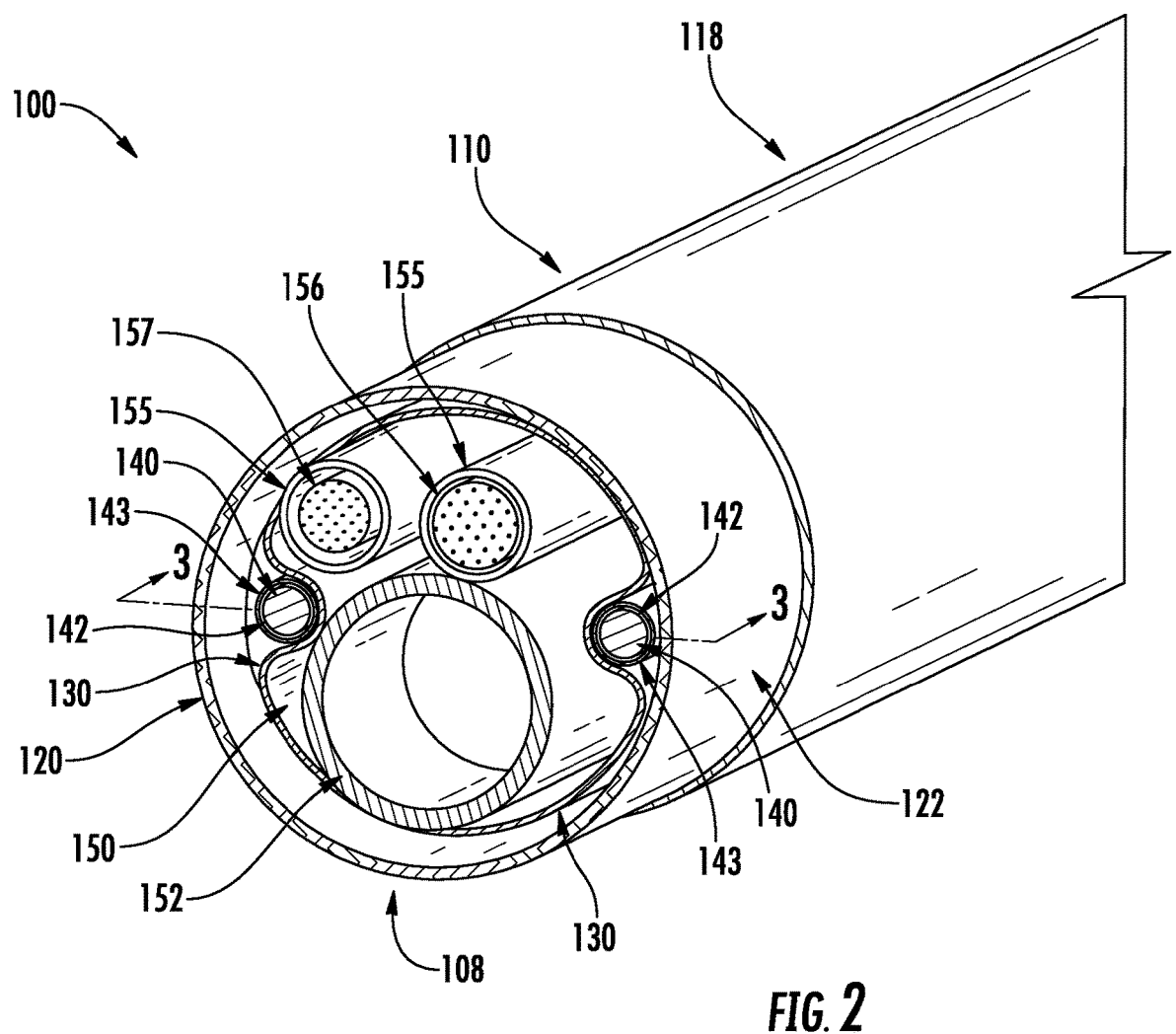
FIG. 2 is a perspective view of the embodiment of FIG. 1.

Turning to FIGS. 2 and 3, the distal end 108 of the endoscope insertion tube 100 is shown without a cap 160. The endoscope insertion tube 100 comprises a tubular shaft 120, preferably comprising an alloy and more preferably comprising a steel alloy. In one preferred embodiment, the shaft 120 comprises flexible braided flat steel wires. Additionally or alternatively, the shaft 120 may comprise wires comprising titanium nickel alloy.

Figure 4:
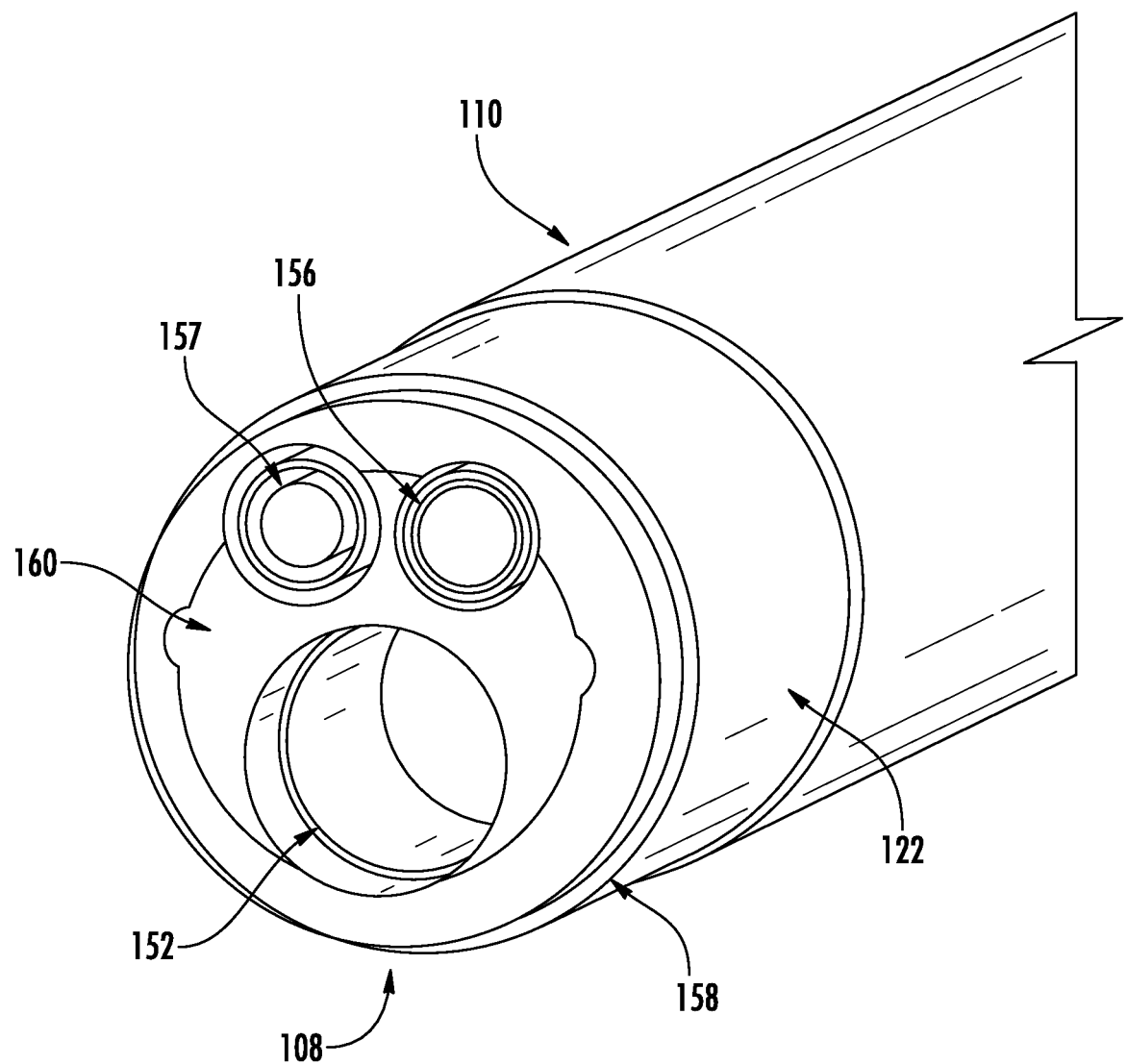
FIG. 4 is a perspective end view of the embodiment of FIG. 1.

In one form, as best seen in FIG. 4, the distal section 118 of the plastic laminate terminates proximate to the distal end 108, leaving an exposed portion 122 of the shaft 120. A marker 158 may be positioned on or near the exposed portion 122. In an alternative form, the distal section 118 may extend to cover the shaft 120 up to the cap 160.

Different durometers and flexibility in two different sections of the endoscope insertion tube 100 may be achieved, for example, by using different thicknesses of the material bonded to an outer surface of the shaft 120. For example, the higher durometer proximal section 112 may have a thermoplastic laminate thickness (and hence outer diameter) that is greater than the thermoplastic laminate thickness (and outer diameter) of the lower durometer distal section 118.

In addition or alternatively, different durometers and flexibility in an intermediate section of the endoscope insertion tube 100 may be achieved by overlapping two neighboring laminate sections. For example, as shown in FIG. 5C, two laminate sections may overlap. FIG. 5C shows a cross-section of an end of middle section 114 overlapping an end of proximal section 112. In some forms, two or more or all of the laminate sections may have at least some overlap with one or both neighboring sections. The order of overlap is reversible, so another form may have an end of section 112 overlapping an end of section 114. If the overlapping laminate sections have different durometers, then the overlapping section may have an intermediate durometer, i.e., less than the higher durometer section and greater than the lower durometer section.

In one form, the endoscope insertion tube 100 comprises a liner 130 having a bonded portion 132 fixed to a portion of an inner surface of the shaft 120 and an unbonded portion 133, which is not fixed to the shaft 120 (see, e.g., FIG. 5, where unbonded portions 133 are proximate to slots 134 of mandrel 135). The interior of the liner 130 may define the boundaries of an inner lumen 150. One or more gaps between the liner 130 and the shaft 120 may be used as deflection channels 142.

Figure 3A:
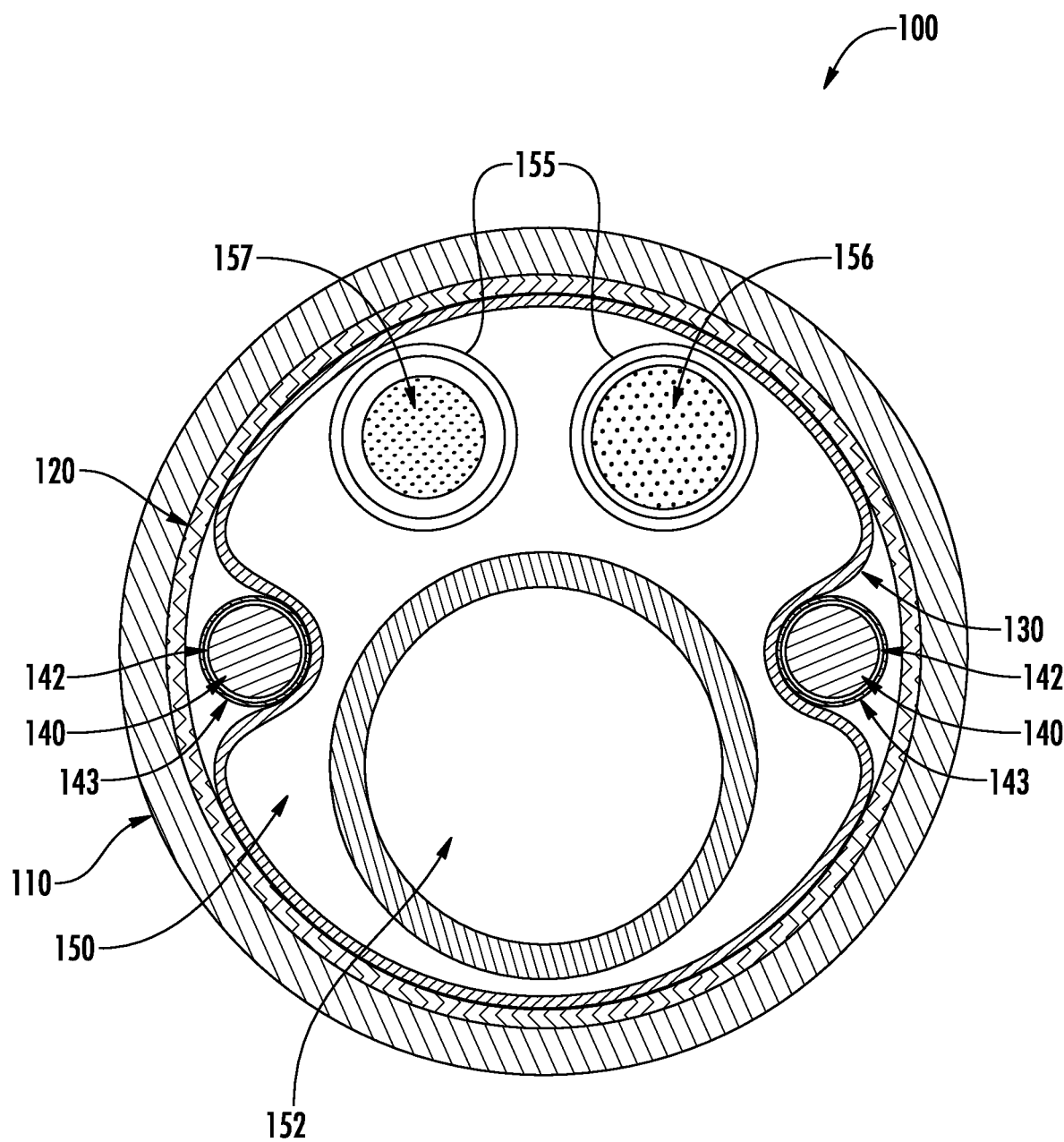
FIG. 3A is a cross-sectional view taken along line 3-3 of FIG. 2.
Figure 3B:
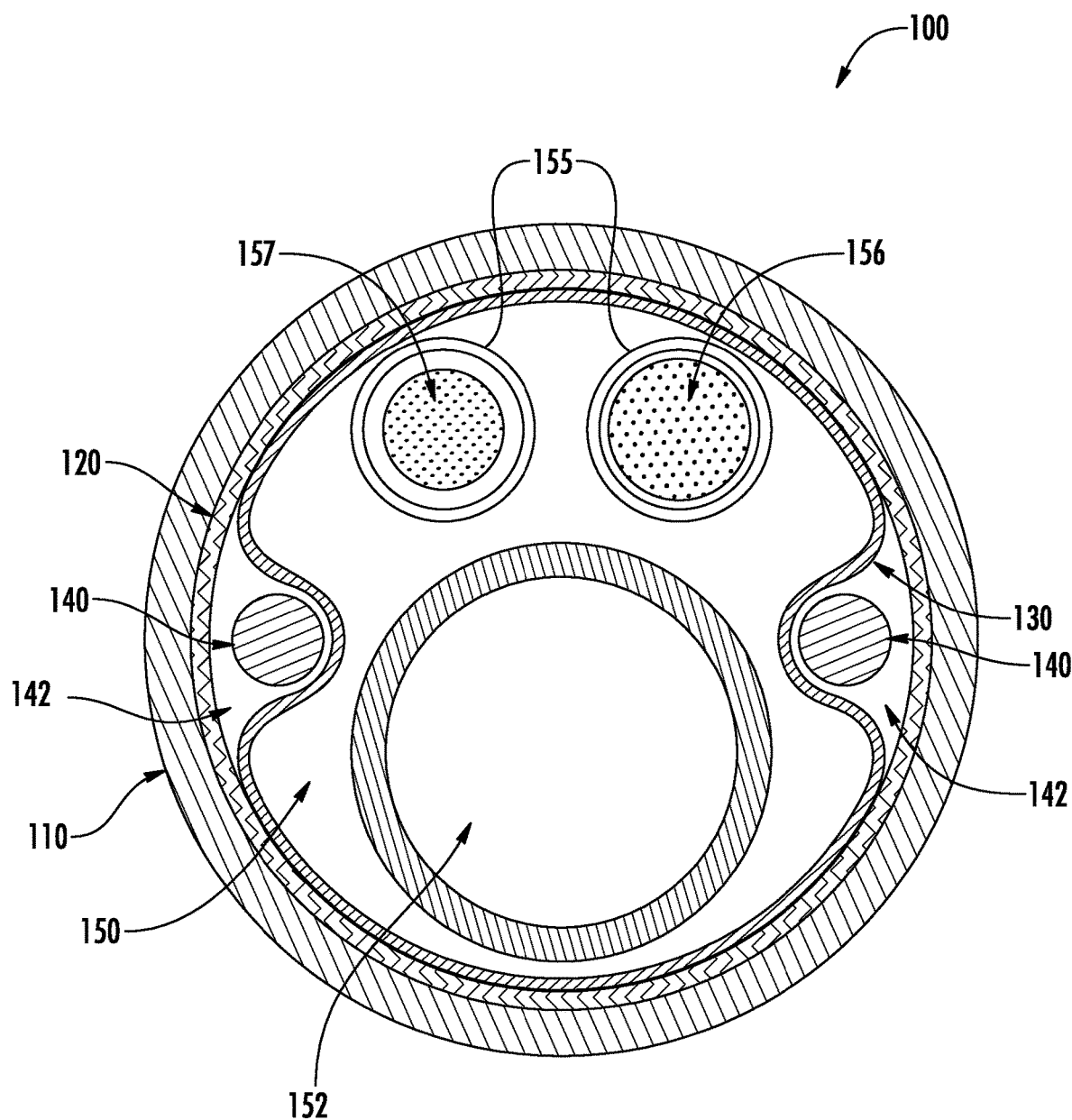
FIG. 3B is a cross-sectional view of another embodiment described herein.

In some forms, as shown in FIGS. 3A and 3B, a shaft liner 130 and one or more gaps between the liner 130 and the shaft are positioned within a lumen (not labeled) of the shaft 120. The shaft liner 130 may have an inner lumen 150.

The shaft 120 comprises a lumen comprising the liner, the space between the shaft liner and the shaft, As shown in FIG. 3B, a deflection wire 140 may be positioned in one or more deflection channel liners 143 or in each of them. The liner 143 may be a plastic or more preferably a thermoplastic, such as PTFE.

Figure 5A:
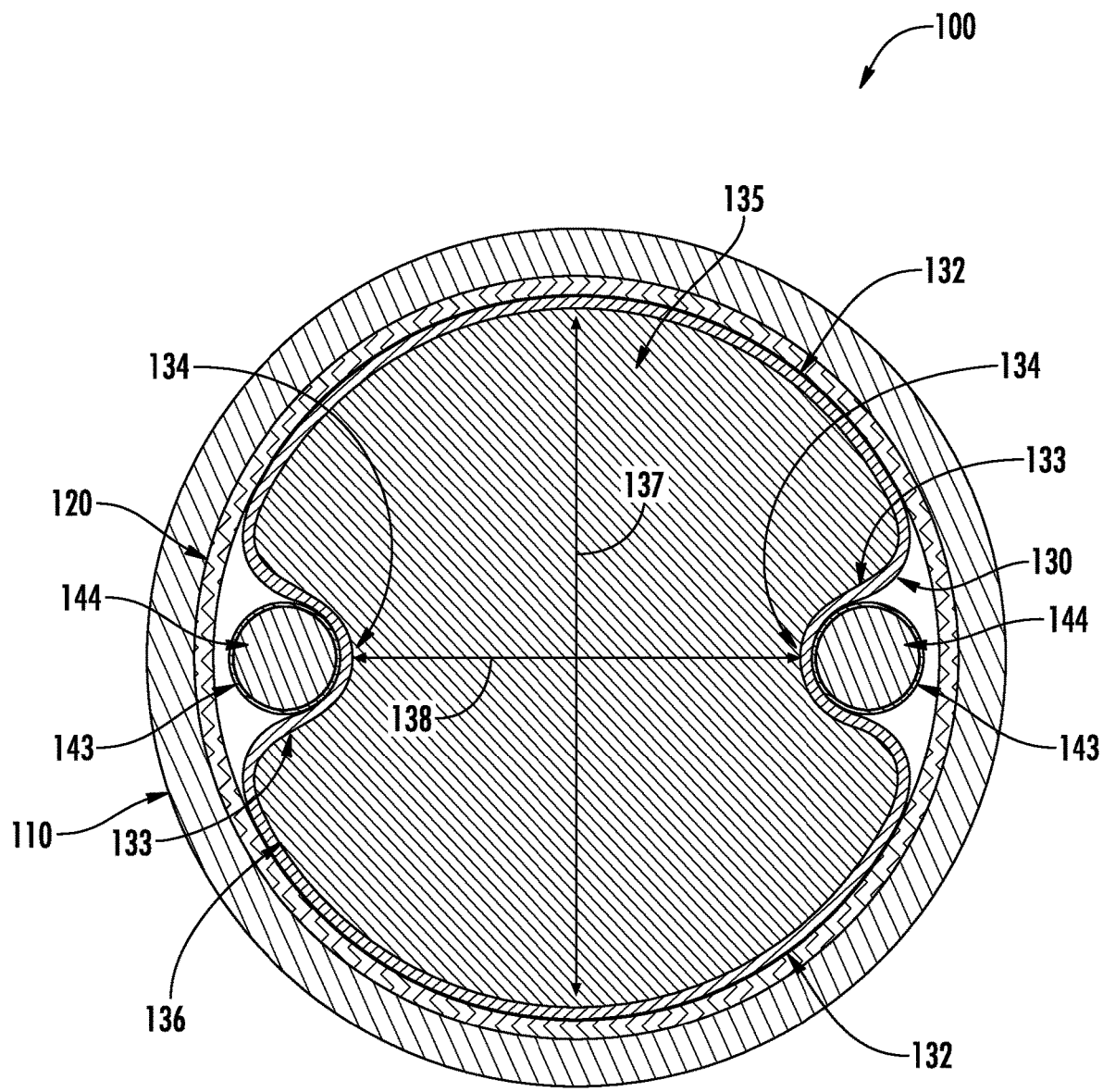
FIG. 5A is a cross-sectional view of another embodiment described herein.

As shown in FIGS. 2, 3A, and 5A, a second liner 143 may be positioned within the gap (between liner 130 and shaft 120), wherein an interior of the second liner 143 may define the deflection channel 142.

A wide range of possibilities exist for what may be positioned within the inner lumen 150, which will depend on the application(s) for which the insertion tube is used. In one form, at least one working channel 152 and at least one optics channel 155 may be positioned within the inner lumen 150. One optics channel 155 may house an imaging optics bundle 156 comprising a complimentary metal-oxide semiconductor ("CMOS") or other suitable image sensor, such as a camera or charge-coupled device sensor. The imaging optics bundle 156 may further comprise a solid core optical fiber connected to the image sensor. One or more optics channels 155 may house one or more light sources, such as an illuminated optical fiber or a light emitting diode ("LED"). Alternatively, an LED may be positioned at the distal end 108 of the shaft without an accompanying optics channel 155. In some embodiments, two working channels 152 may be positioned within the inner lumen 150.

Preferred embodiments, in which wall thickness has been minimized by positioning deflection wires 140 within the lumen 150 of the shaft 120, allow an efficient use of space within the lumen 150. The outer diameter of the insertion tube 100 may be the size of typical ureteroscopes (e.g., 2-3 mm), but full-sized optical components and working channel 152 may be used. Smaller optics may produce an inferior image and a smaller working channel may not allow for use of common tools and may also slow irrigation flow.

Turning to FIG. 4, an endoscope insertion tube 100 may comprise a marker 158 and cap 160. The marker 158 may comprise a material that is radio opaque, such as a high density metal. One or more markers 158 may be positioned anywhere along the length of the endoscope insertion tube 100; one preferable location is proximate to the distal end 108 of the endoscope insertion tube 100, so that users are able to visualize or otherwise detect the approximate location of the distal end 108 within a patient.

The cap 160 may be attached, such as by welding or other suitable means, to the distal ends of the deflection wires 140. In some embodiments, the deflection channels 142 are not in fluid communication with the lumen 150. The cap 160 may comprise one or more apertures for the distal ends of the working channel 152 and optics channels 155 to interface with the environment proximate to the distal end 108 of the endoscope insertion tube 100.

In some forms, the marker 158 and optics channels 155 are about 3-4 mm or less in length. The length of the rigid marker 158 is preferably minimized because it enlarges the deflection tangent of a preferentially bendable portion (e.g., sections 114, 116, and 118) of the insertion tube 100.

Figure 6B:
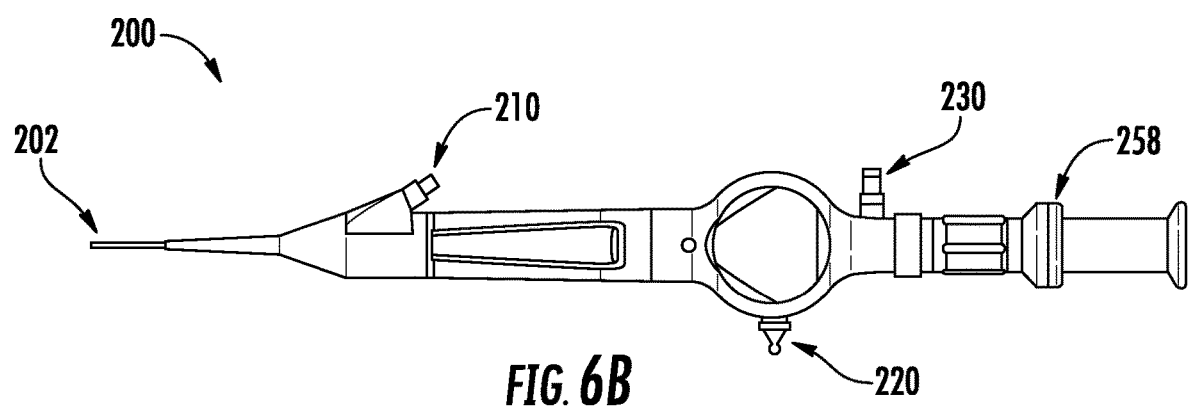
FIG. 6B is a side elevation view of a handle 200.

FIG. 6 shows a handle 200 for steering the insertion tube 100. In one embodiment, the handle 200 comprises a tip 202, luer lock 210, and trigger 220. A tip 202 of the handle 200 connects to the proximal end 106 of endoscope insertion tube 100. A trigger 220 actuates the deflection wires 140.

The handle 200 may also comprise a light pin 230, imaging optics bundle termination 256, and eyepiece 258. A light pin 230 illuminates the one or more illuminating optics bundles 157. The images captured and transmitted through the imaging optics bundle 156 are displayed on an eyepiece 258, which is connected to an imaging optics bundle termination 256. The eyepiece 258 may be removable or permanently attached.

One embodiment of the invention is a method of making an endoscope insertion tube 100 using a mandrel 135. As shown in FIG. 5, a primary mandrel 135, a liner 130, and two secondary mandrels 141 may be inserted into a shaft 120.

Figure 5B:
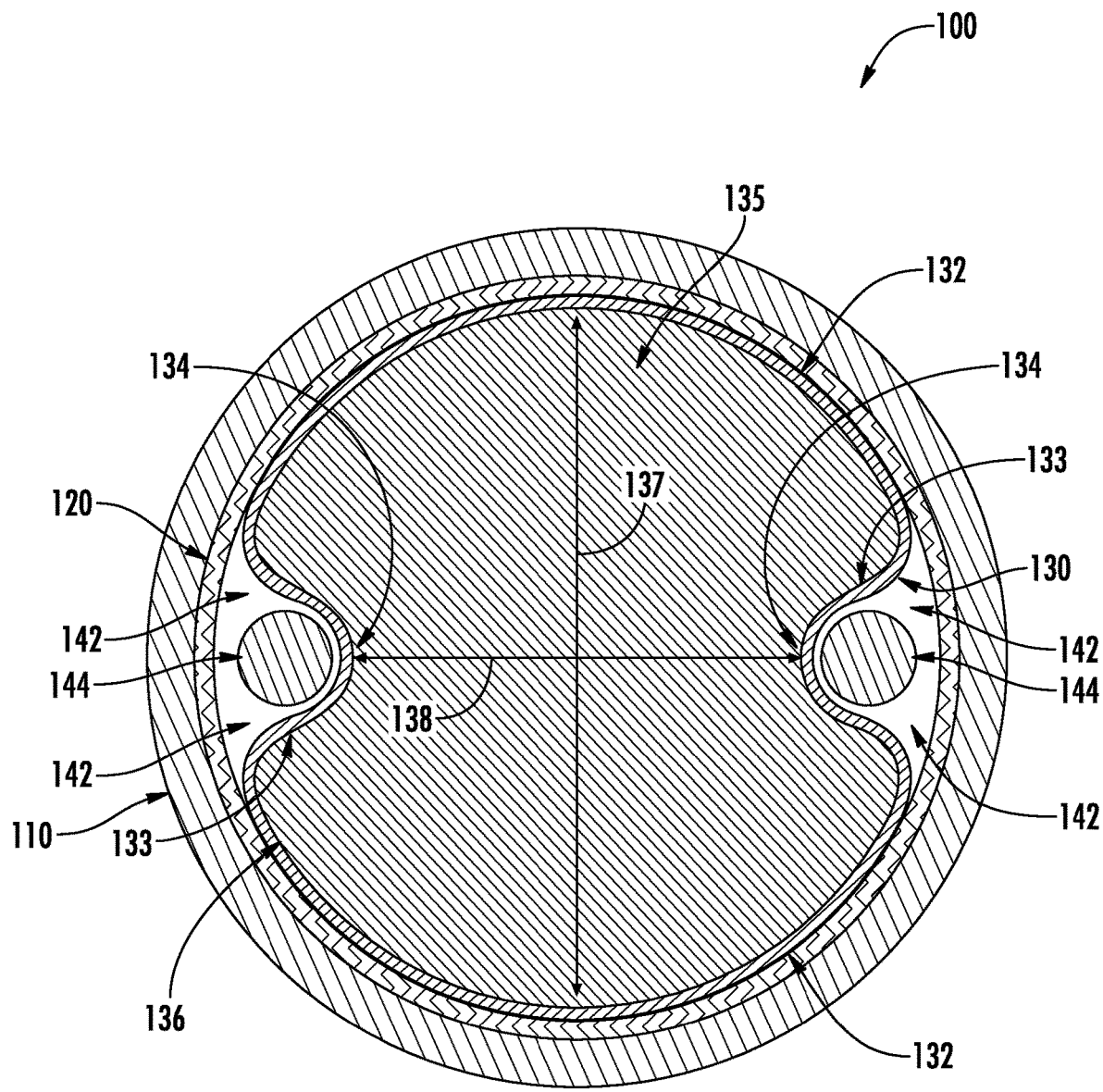
FIG. 5B is a cross-sectional view of another embodiment described herein.
Figure 5C:
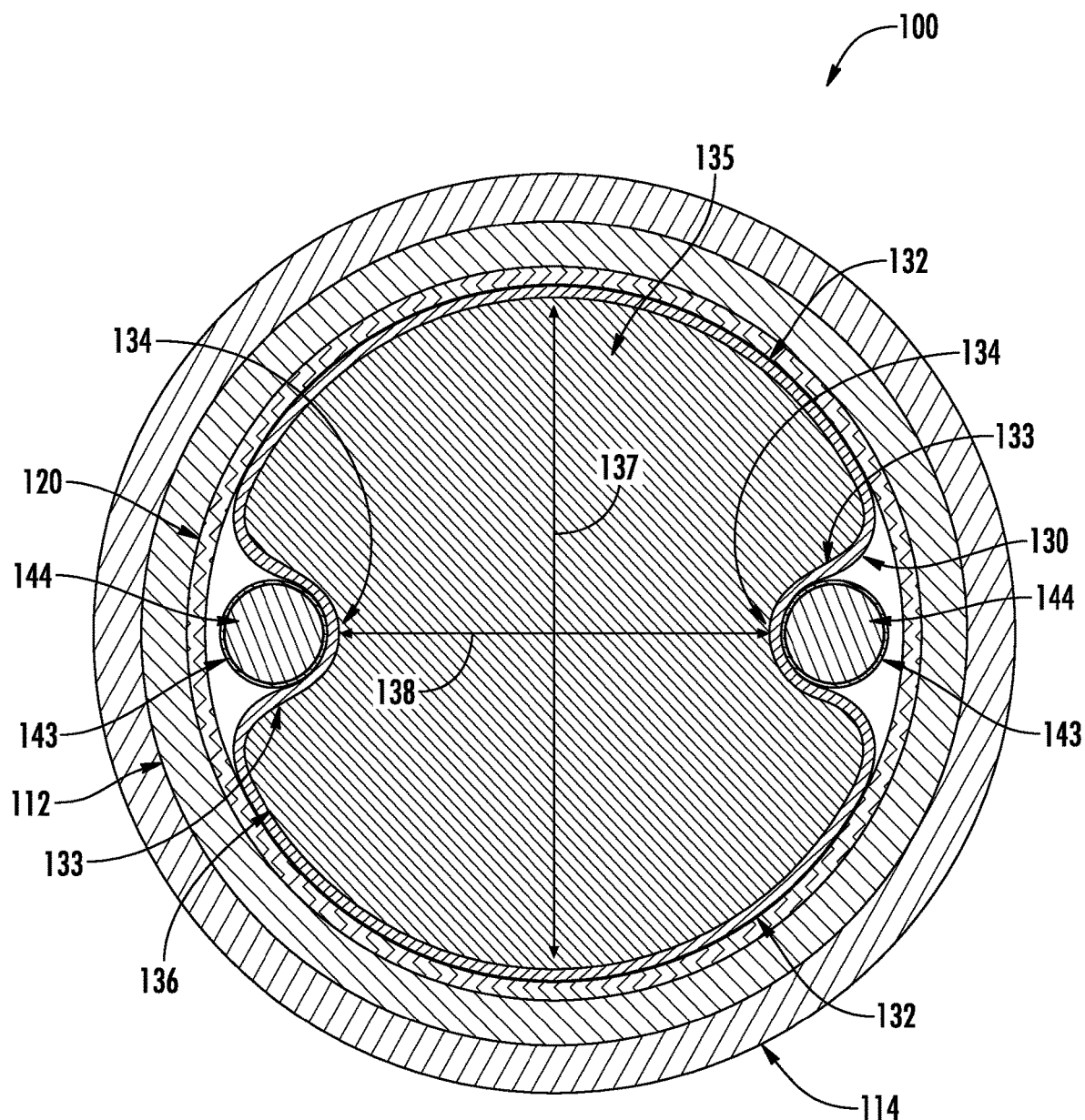
FIG. 5C is a cross-sectional view of another embodiment described herein.

In some forms, as shown in FIGS. 5A-C, the mandrel 135 may have two slots 134 on opposing sides of the mandrel. Each slot 134 is preferably a concave groove or indentation along at least a portion of the length of the mandrel, wherein the slot 134 is sized to form a deflection channel 142 between the liner 130 and shaft 120 that can accept a deflection wire 140. In alternative forms, the mandrel 135 may have only one slot 134 or two, three, four, or more slots 134, corresponding to a predetermined number of deflection channels 142 for deflection wires 140. For a mandrel 135 with plural slots 134, they may be spaced regularly or irregularly across the circumference of the mandrel 135. In some forms, one or more slots 134 may be shaped to substantially conform to at least a portion of the exterior of secondary mandrels 144. One or more secondary mandrels 144 may be nested within a slot 134 (see, e.g., FIG. 5A).

In addition or alternatively, the height 137 and/or width 138 of the cross-section of the mandrel 135 could vary along its length. In one preferred embodiment, for example, the width (i.e., diameter across one or more slots 134) may be a certain value along the higher durometer proximal section 112 and the width be less at one or more of the middle and distal sections 114, 116, 118. The width 138 of the mandrel 135 is preferably measured at the base of slots 134 (see arrows for feature 138 in FIGS. 5A-C). In this form, the sections 114, 116, 118 will have enhanced preferential deflection relative to section 112. In addition or alternatively, the height 137 may be a certain value at a section of the proximal section 112 and the height 137 may be greater at one or more of the middle and distal sections 114, 116, 118. These forms may also have an enhanced deflection tangent for the distal end 108 of the insertion tube 100.

In addition or alternatively, the depth of the slot 134 may vary at different sections along the length of the mandrel 135, creating a variable cross section. This variable cross section could impart a variable moment of inertia (i.e., resistance to bending) to the insertion tube 100. In one form, the mandrel 135 may have deeper slots 134 at a section near the proximal end 106 of endoscope insertion tube 100, which may permit the proximal ends of deflection wires 140 to be positioned proximate to a center point of the inner lumen 150. The mandrel 135 may also have shallower slots 134 at a section near the distal end 108 of the endoscope insertion tube 100, which may permit the distal ends of deflection wires 140 to be positioned farther from the center point of the inner lumen 150. In addition or alternatively, this configuration may enhance the effect of the variable durometer laminate on the middle and distal sections 114, 116, 118 of the insertion tube 100.

Secondary mandrels 141 are positioned between the shaft 120 and the liner 130 to keep open what will become the deflection channels 142.

As shown in FIGS. 1, 2, and 5C one or more laminate sections 110 may be positioned over the shaft 120. One preferred method of bonding plastic laminate 110 to the shaft 120 is through the use of an additional heat shrinkable tube (not shown) comprising any suitable thermoplastic material, such as fluorinated ethylene-propylene ("FEP"). Once the plastic laminate sections 110 are in position around outside surface of the shaft 120, the tube is positioned around the sections 110.

The primary mandrel 135, liner 130, secondary mandrels 141, shaft 120, laminate sections 110, and shrink tube may be heated to bond the shaft 120 to the liner 130 and laminate sections 110. A laminator may be used to apply dry heat forced air convection over the insertion tube assembly. The temperature and time may vary according to the differing durometers of each section of the insertion tube 100. The heat may simultaneously shrink the outer tube and melt the plastic layer(s). If a shrink tube is used, it is removed after the insertion tube assembly cools.

In an alternative form, a plastic housing 110 may be cast on the exterior of the shaft 120. Casting a plastic housing 110 onto shaft 120 may be achieved by emerging the shaft 120 into liquid plastic, such as a molten thermoplastic, thereby adding thin layers (each less than about 0.01-0.1 mm) until a desired thickness is achieved.

In some forms, the shaft 120 comprises braided wire, such as steel or an alloy thereof, and the plastic laminate sections 110 may be laminated to the shaft 120. The plastic laminate 110 may at least partially melt into and/or through interstices of the braided shaft 120 and may attach to the shaft liner 130, fixing at least a portion of the shaft liner 130 to the inner surface of the shaft 120. The melted plastic laminate 110 may also attached to one or more deflection channel liners 143. The melted plastic laminate 110 may also file most of the gap around and between the mandrels 144 (see FIGS. 5A-C) and the shaft 120.

The braid may have a variable PIC rate (i.e., rotations of braid per centimeter) such that it is more rigid in the proximal section 112 than one or more of the other sections 114, 116, 118. In addition or alternatively, the braid may be reinforced with a coil (not shown). In addition or alternatively, the braid may be electroplated over at least section 112 to further increase its rigidity. In some forms, the braid may not be electroplated except for section 112.

In addition or alternatively, heating the plastic laminate sections 110 melts and bonds the plastic laminate 110 to the shaft 120 without a heat shrinkable tube.

During the heating step, at least a bonded portion 132 of the liner 130 bonds to an inner surface of the shaft 120 and an unbonded portion 133 is separated from the inner surface of the shaft 120 by the secondary mandrel 141, creating a gap that may be used as a deflection channel 142.

In some embodiments, the primary mandrel 135 may be coated with PTFE, which will coat the inner lumen 150.

In operation, an endoscope insertion tube 100 is connected to a handle 200. The proximal section 112, which in some embodiments may form most of the length of insertion tube 100, may be coiled in packaging. The insertion tube 100 may be uncoiled and proximal optical connections (not shown) to the imaging optics bundle 156 and illumination optics bundle 157 may be operably connected, through the handle 200, to the eyepiece 258 and light pin 230, respectively. The working channel 152 may be connected to irrigation.

In one application, the endoscope insertion tube 100 may be back loaded on a guide wire that is placed with a cystoscope or introduced to the ureter using an access sheath. To locate abnormalities, such as a kidney stone, the insertion tube 100 may be guided through the renal collecting system using the imaging provided by imaging means and x-ray imaging provided by fluoroscopy. A variety of small tools can be passed through the working channel. For example, a laser may be used to break the stone or it may be removed with a basket.

The embodiments and examples shown in the drawings and described above are exemplary of numerous others that may be made within the scope of the appended claims. It is contemplated that numerous other configurations may be used, and the material of each component may be selected from numerous materials other than those specifically disclosed.

No special definition of a term or phrase, i.e., a definition that is different from the ordinary and customary meaning as understood by those skilled in the art, is intended to be implied by consistent usage of the term or phrase herein. The words and phrases used herein should be understood and interpreted to have a meaning consistent with the understanding of those words and phrases by those skilled in the relevant art. For example, an embodiment comprising a singular element does not disclaim plural embodiments; i.e., the indefinite articles "a" and "an" carry either a singular or plural meaning and a later reference to the same element reflects the same potential plurality. A structural element that is embodied by a single component or unitary structure may be composed of multiple components. Ordinal designations (first, second, third, etc.) merely serve as a shorthand reference for different components and do not denote any sequential, spatial, or positional relationship between them. Words of approximation such as "about," "approximately," or "substantially" refer to a condition or measurement that, when so modified, is understood to not necessarily be absolute or perfect but would be considered close enough by those of ordinary skill in the art to warrant designating the condition as being present or the measurement being satisfied. For example, a numerical value or measurement that is modified by a word of approximation, such as "about" or "approximately," may vary from the stated value by 1, 2, 3, 4, 5, 6, 7, 10, 12, and up to 15%.

The foregoing description of the embodiments of the invention has been presented for purposes of illustration and description. It is not intended to be exhaustive or to limit the invention to the precise form(s) disclosed, and modifications and variations are possible in light of the above teachings or may be acquired from practice of the invention. The embodiments were chosen and described in order to explain the principles of the invention and its practical application to enable one skilled in the art to utilize the invention in various embodiments and with various modifications as are suited to the particular use contemplated. It is intended that the scope of the invention be defined only by the following claims, as amended, and their equivalents.

DESCRIPTION OF REFERENCED NUMERALS

10 . . . flexible endoscope
100 . . . endoscope insertion tube
102 . . . neutral position
104 . . . deflected position
106 . . . proximal end of endoscope insertion tube 100
108 . . . distal end of endoscope insertion tube 100
110 . . . thermoplastic laminate
111 . . . laminate section
112 . . . higher durometer proximal section
114 . . . intermediate durometer middle section
116 . . . higher durometer middle section
118 . . . lower durometer distal section
120 . . . shaft
122 . . . exposed portion of shaft
130 . . . shaft liner
132 . . . bonded portion of liner 130
133 . . . unbonded portion of liner 130
134 . . . slot of mandrel 135
135 . . . primary mandrel
136 . . . surface of mandrel 135
137 . . . height of mandrel 135
138 . . . width of mandrel 135
140 . . . deflection wire
142 . . . deflection channel
143 . . . deflection channel liner
144 . . . secondary mandrel
150 . . . inner lumen of shaft liner 130
152 . . . working channel
155 . . . optics channel
156 . . . imaging optics bundle
157 . . . illuminating optics bundle
158 . . . marker
160 . . . cap
200 . . . handle
202 . . . tip
210 . . . luer lock
220 . . . trigger 230 ... light pin
256 ... imaging optics bundle termination
258 ... eyepiece

What is claimed is:

1. An endoscope insertion tube comprising:
a shaft having an outer surface, an inner surface, a proximal end, a distal end, and a lumen;
a plastic housing fixed to at least a portion of the outer surface of the shaft;
a shaft liner, wherein an inner surface of the shaft liner defines a single inner lumen and wherein at least a portion of an outer surface of the shaft liner is fixed to the inner surface of the shaft;
a working channel and optics positioned in the inner lumen of the shaft liner;
at least one gap between the shaft and the shaft liner; and
a deflection wire, wherein at least a portion of the deflection wire is positioned within the gap such that said portion of the deflection wire is within the lumen of the shaft and exterior to the inner lumen of the shaft liner,
the plastic housing comprising a first section having at least a first durometer, a second section having at least a second durometer, a third section having at least a third durometer, and a fourth section having at least a fourth durometer;
wherein at least a portion of the first section is proximate to a proximal end of the shaft and wherein at least a portion of the fourth section is proximate to a distal end of the shaft;
wherein the fourth section is distal to the third section and the third section is distal to the second section;
wherein the fourth durometer is less than the first durometer, the second durometer, and the third durometer; and
wherein the second durometer is less than the first durometer and the third durometer; and
wherein the shaft has a length and comprises a braided material having a variable PIC rate, defined as a number of rotations of braid per centimeter along the length of the shaft, and the shaft has first, second, third, and fourth portions corresponding to the first, second, third, and fourth sections of the plastic housing, and wherein the first portion of the shaft has a PIC rate that is different than PIC rates of the second, third, and fourth portions.

2. The endoscope insertion tube of claim 1, wherein the shaft liner has a substantially uniform thickness.

3. The endoscope insertion tube of claim 1, wherein the inner lumen of the shaft liner is hollow.

4. An endoscope insertion tube comprising:
a braided shaft having an inner surface and a lumen;
a shaft liner having an inner lumen, wherein at least a portion of the shaft liner is fixed to the inner surface of the shaft;
a working channel and optics positioned in the inner lumen of the shaft liner;
at least two deflection wires, wherein at least a portion of each deflection wire is positioned within the lumen of the shaft and exterior to the inner lumen of the shaft liner;
a thermoplastic laminate laminated to at least a portion of the outer surface of the shaft, the thermoplastic laminate comprising:
a first section having at least a first durometer, a second section having at least a second durometer, a third section having at least a third durometer, and a fourth section having at least a fourth durometer;
wherein at least a portion of the first section is proximate to a proximal end of the shaft and wherein at least a portion of the fourth section is proximate to a distal end of the shaft;
wherein the fourth section is distal to the third section and the third section is distal to the second section;
wherein the fourth durometer is less than the first durometer, the second durometer, and the third durometer; and
wherein the second durometer is less than the first durometer and the third durometer; and
wherein the shaft has a length and comprises a braided material having a variable PIC rate, defined as a number of rotations of braid per centimeter along the length of the shaft, and the shaft has first, second, third, and fourth portions corresponding to the first, second, third, and fourth sections of the thermoplastic laminate laminated to the outer surface of said sections of the shaft, and wherein the first portion of the shaft has a PIC rate that is different than PIC rates of the second, third, and fourth portions.

5. The endoscope insertion tube of claim 4, wherein the shaft liner has a thickness, defined by a greatest difference between an outer diameter of the shaft liner and an inner diameter of the shaft liner at the portions of the shaft liner fixed to the shaft, that is about less than or equal to a thickness of the shaft.

6. The endoscope insertion tube of claim 4, wherein the inner lumen of the shaft liner is hollow.

7. The endoscope insertion tube of claim 4, further comprising: a light source, an image sensor, and a handle, wherein the handle is attached to a first end of the shaft and operably coupled to the deflection wires, wherein the light source and image sensor are positioned proximate to a distal end of the shaft, and wherein the image sensor comprises an analog sensor.

8. The endoscope insertion tube of claim 7, wherein the image sensor comprises electrical lines coupled to an analog-to-digital converter, wherein at least a portion of the electrical lines are positioned within the inner lumen of the shaft liner, and wherein the analog-to-digital converter is positioned proximate to the first end of the shaft.

9. The endoscope insertion tube of claim 4, further comprising at least four gaps between the shaft and shaft liner and at least four tubular deflection channel liners positioned within the gaps.

10. The endoscope insertion tube of claim 4, wherein the inner lumen of the shaft liner is non-circular.

11. The endoscope insertion tube of claim 4, wherein the inner lumen of the shaft liner has plural indentations.

12. The endoscope insertion tube of claim 4, further comprising a cap attached to a distal end of the shaft, wherein the at least two deflection wires are attached to the cap.

13. The endoscope insertion tube of claim 1, further comprising:
the shaft liner has at least two bonded sections and at least two unbonded sections, wherein at least two bonded sections are fixedly attached to at least a portion of the inner surface of the shaft;
at least a second gap, wherein one gap is between the shaft and each of at least two unbonded sections of the shaft liner;
wherein an interior of the shaft liner defines a non-circular inner lumen;
at least two deflection channel liners, wherein one deflection channel liner is positioned in each of at least two gaps, and wherein an interior of each deflection channel liner defines a deflection channel;

at least a second deflection wire, wherein each deflection wire has a proximal end and a distal end, wherein at least a portion of the at least two deflection wires are positioned in each of at least two deflection channels;

wherein at least a portion of at least two deflection wires are positioned within the lumen of the shaft and exterior to the inner lumen of the shaft liner;

at least two optics channels positioned within the inner lumen proximate to the distal end of the shaft;

at least a portion of at least one light source positioned within an optics channel and proximate to a distal end of the endoscope insertion tube;

at least a portion of at least one image sensor positioned within an optics channel and proximate to the distal end of the endoscope insertion tube; and a cap attached to the distal end of the at least two deflection wires.

* * * * *